(12) United States Patent
Minev et al.

(10) Patent No.: US 10,695,555 B2
(45) Date of Patent: Jun. 30, 2020

(54) SYNTHETIC SKIN FOR RECORDING AND MODULATING PHYSIOLOGICAL ACTIVITIES

(71) Applicant: ECOLE POLYTECHNIQUE FEDERALE DE LAUSANNE (EPFL), Lausanne (CH)

(72) Inventors: Ivan Rusev Minev, Lausanne (CH); Arthur Hirsch, Lausanne (CH); Pavel Musienko, St. Petersburg (RU); Grégoire Courtine, Lausanne (CH); Stephanie P. Lacour, Daillens (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 312 days.

(21) Appl. No.: 15/542,042

(22) PCT Filed: Jan. 8, 2016

(86) PCT No.: PCT/EP2016/050270
§ 371 (c)(1),
(2) Date: Jul. 6, 2017

(87) PCT Pub. No.: WO2016/110564
PCT Pub. Date: Jul. 14, 2016

(65) Prior Publication Data
US 2018/0001081 A1    Jan. 4, 2018

(30) Foreign Application Priority Data
Jan. 8, 2015    (WO) ................. PCT/EP2015/050274

(51) Int. Cl.
*A61N 1/05*    (2006.01)
*A61B 5/04*    (2006.01)
(Continued)

(52) U.S. Cl.
CPC ........ *A61N 1/0531* (2013.01); *A61B 5/04001* (2013.01); *A61B 5/0478* (2013.01);
(Continued)

(58) Field of Classification Search
CPC .... A61N 1/0531; A61N 1/375; A61N 1/0551; A61N 1/0553; H01L 23/49811;
(Continued)

(56) References Cited

U.S. PATENT DOCUMENTS

| 8,332,053 | B1 | 12/2012 | Patterson et al. |
| 2003/0097166 | A1 | 5/2003 | Krulevitch et al. |
| 2013/0303873 | A1 | 11/2013 | Vörös et al. |

FOREIGN PATENT DOCUMENTS

WO    2015/172894 A1    11/2015

OTHER PUBLICATIONS

Minev, I. R. et al., "High sensitivity recording of afferent nerve activity using ultra-compliant microchannel electrodes: an acute in vivo validation," J. Neural Eng. 9:1-7, 2012.
(Continued)

*Primary Examiner* — Mark Bockelman
(74) *Attorney, Agent, or Firm* — Seed Intellectual Property Law Group LLP

(57) ABSTRACT

A method produces a device adapted to be implanted into the human body for purposes such as neural stimulation, sensing or the like. The method includes: providing a stretchable layer or membrane of an insulating material; forming on the layer or membrane at least one stretchable conductive path; depositing at least one small bolus of a soft and conductive paste or material onto pre-defined areas or portions of the at least one conductive path, and inserting a first end portion of a conductive element 71 into the at least one bolus of soft conductive paste or material. A second end portion of the
(Continued)

conductive element opposite to the first end portion is not inserted into the at least one bolus.

22 Claims, 27 Drawing Sheets

(51) Int. Cl.
*A61N 1/375* (2006.01)
*A61B 5/0478* (2006.01)
*H01L 23/498* (2006.01)
*H05K 3/28* (2006.01)
*H05K 1/02* (2006.01)
*H01L 23/13* (2006.01)

(52) U.S. Cl.
CPC ........... *A61N 1/0551* (2013.01); *A61N 1/375* (2013.01); *H01L 23/4985* (2013.01); *H01L 23/49811* (2013.01); *A61B 2562/028* (2013.01); *A61B 2562/046* (2013.01); *A61B 2562/125* (2013.01); *A61B 2562/164* (2013.01); *A61N 1/0553* (2013.01); *H01L 23/13* (2013.01); *H01L 23/49838* (2013.01); *H01L 2924/0002* (2013.01); *H05K 1/0272* (2013.01); *H05K 1/0283* (2013.01); *H05K 3/284* (2013.01); *H05K 2201/0133* (2013.01); *H05K 2201/0314* (2013.01)

(58) Field of Classification Search
CPC ......... H01L 2924/0002; H01L 23/4985; H01L 23/49838; H01L 23/13; A61B 5/04001; A61B 5/0478; A61B 2562/164; A61B 2562/125; A61B 2562/046; A61B 2562/028; H05K 1/0283; H05K 1/0272; H05K 3/284; H05K 2201/0314; H05K 2201/0133
See application file for complete search history.

(56) References Cited

OTHER PUBLICATIONS

Minev, I. R. et al., "Evaluation of an Elastomer Based Gold Microelectrode Array for Neural Recording Applications," Proceedings of the 5$^{th}$ International IEEE EMBS Conference on Neural Engineering, Cancun, Mexico, Apr. 27-May 1, 2011, pp. 482-485.
Robinson, A. et al., "Hybrid stretchable circuits on silicone substrate," Journal of Applied Physics 115, 5 pgs., 2014.

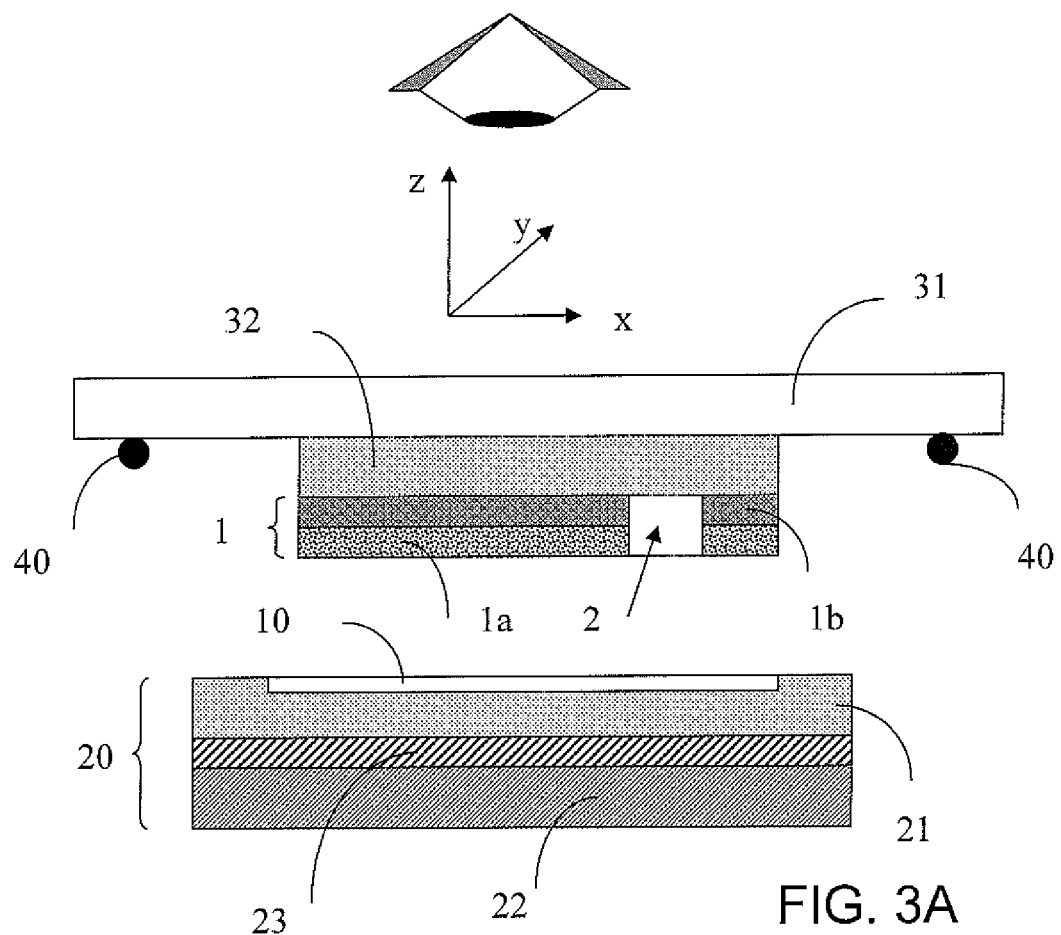
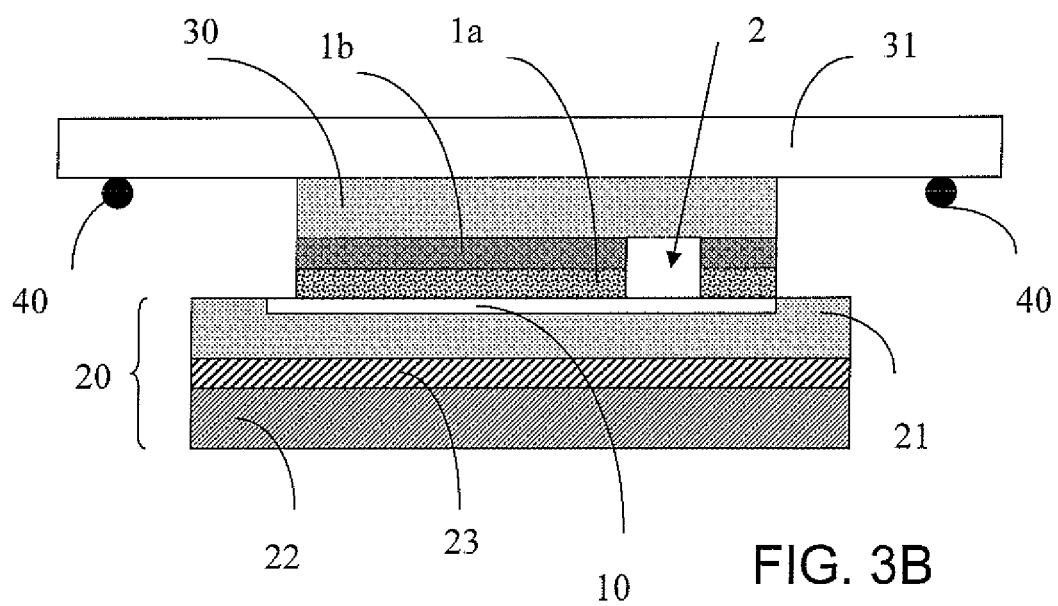

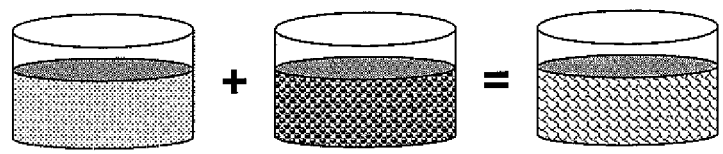
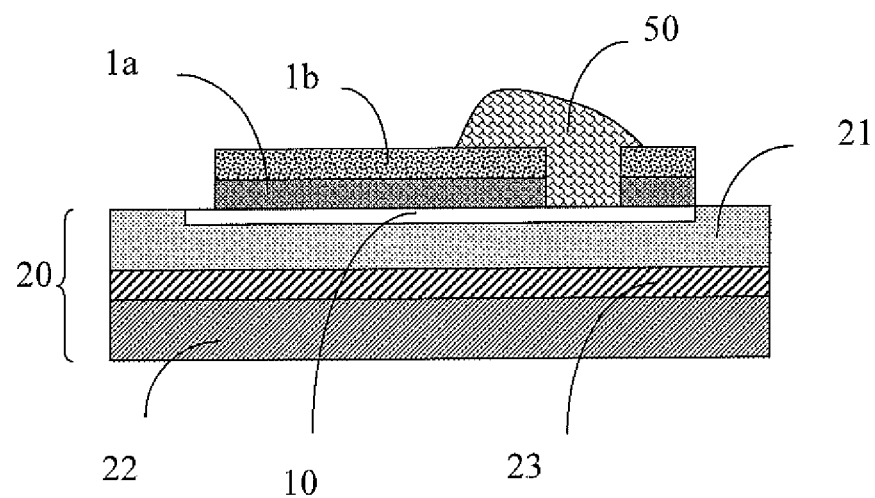
FIG. 5A
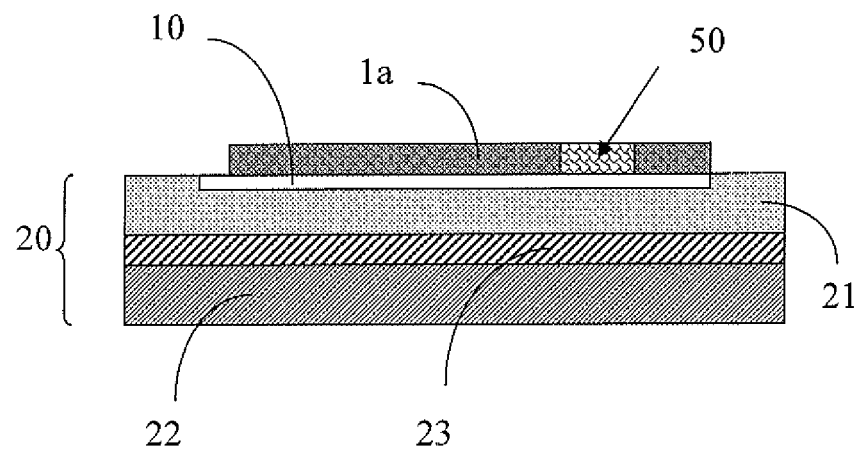
FIG. 5B

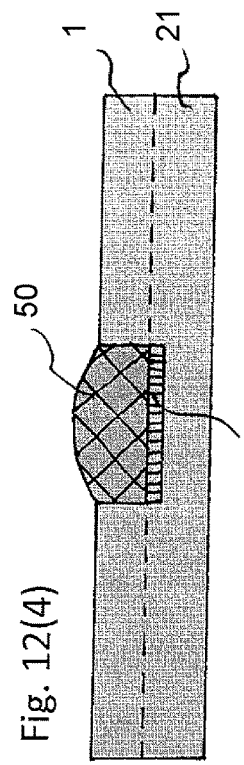
Fig. 9
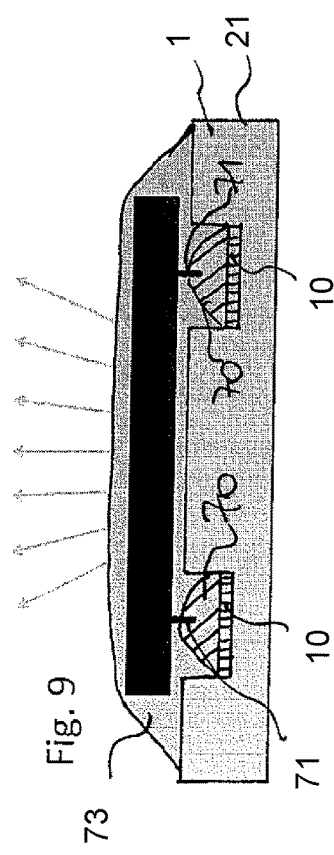
Fig. 12(1)
Fig. 12(2)
Fig. 12(3)
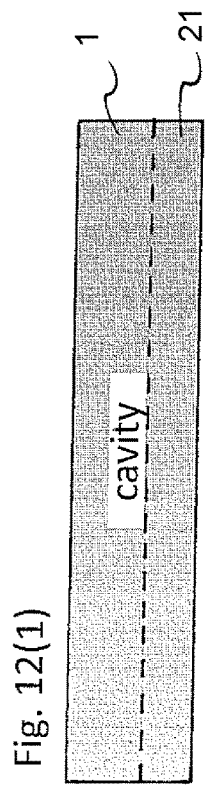
Fig. 12(4)
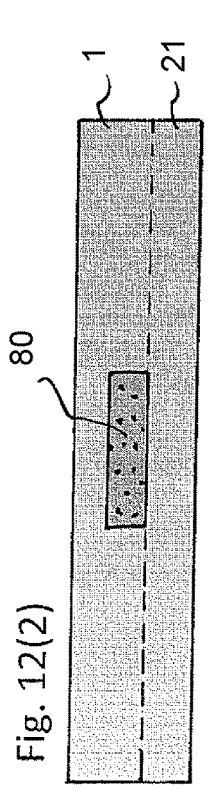
Fig. 12(5)
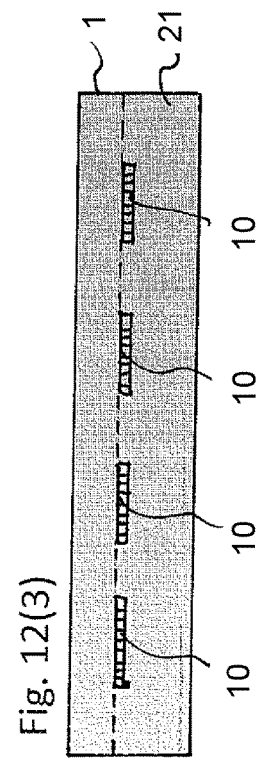
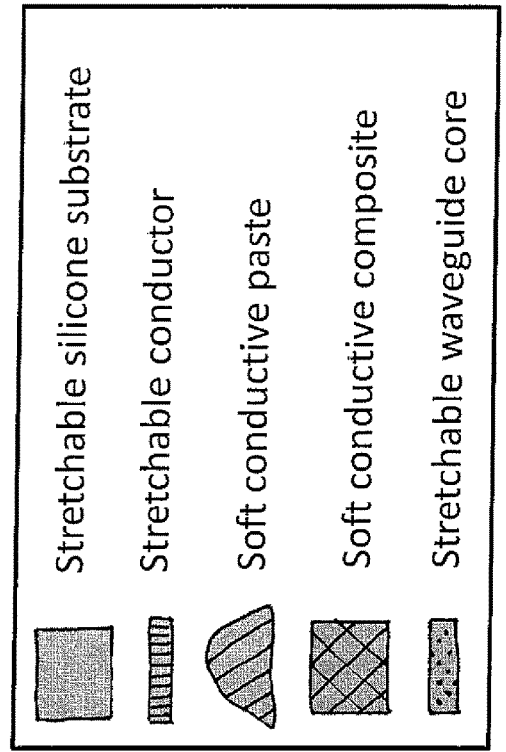

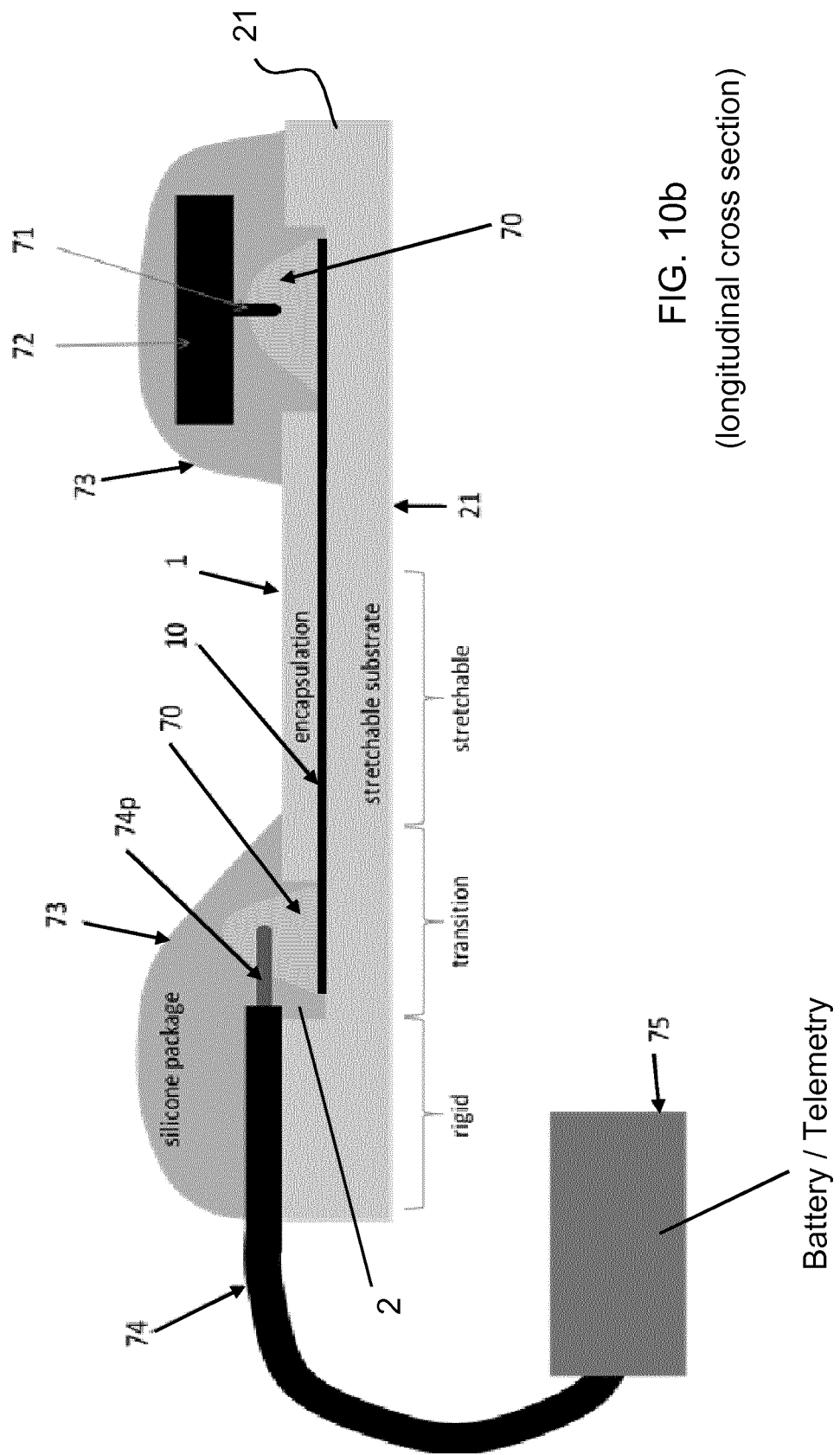
FIG. 10b (longitudinal cross section)

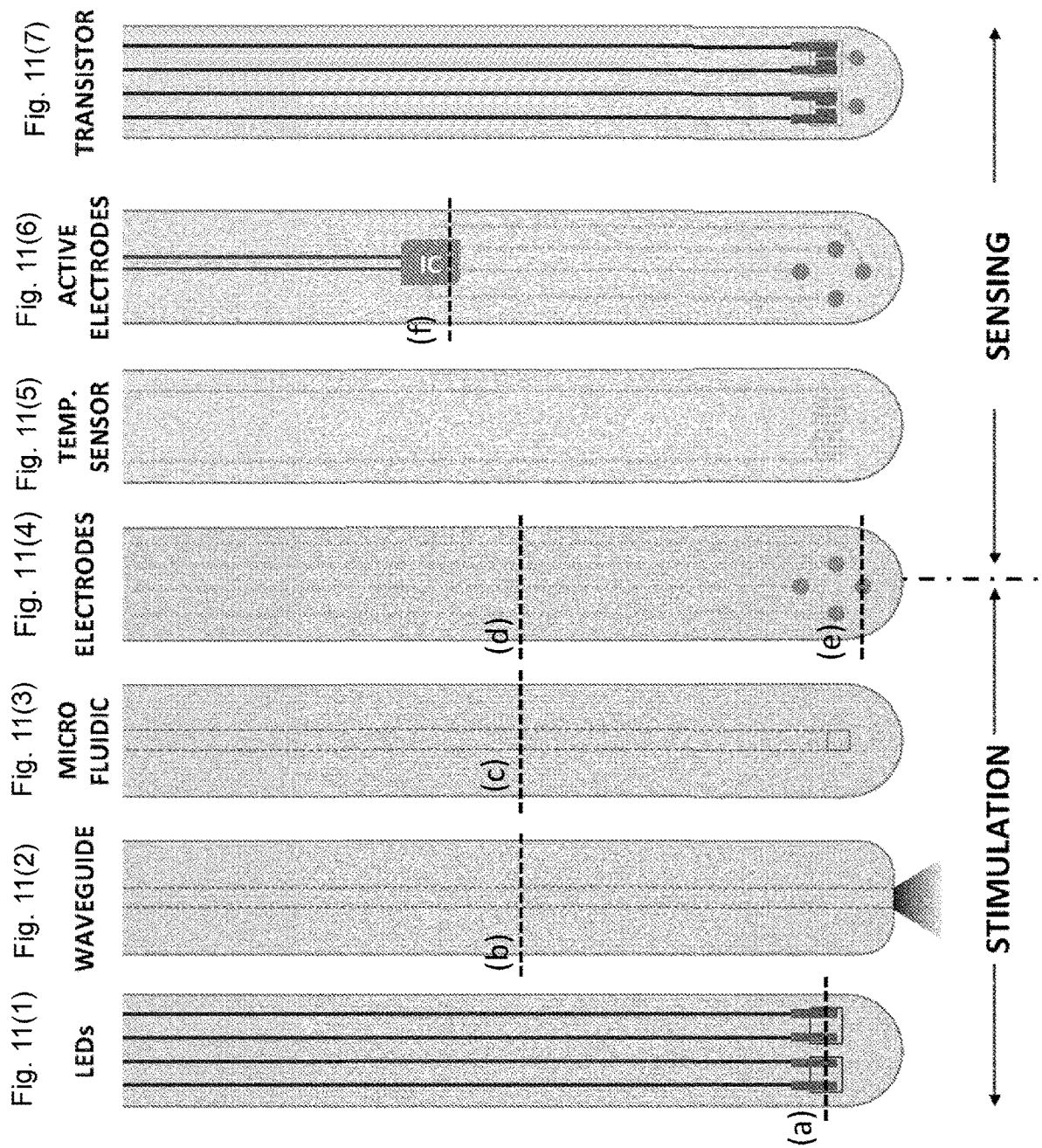

FIG. 15
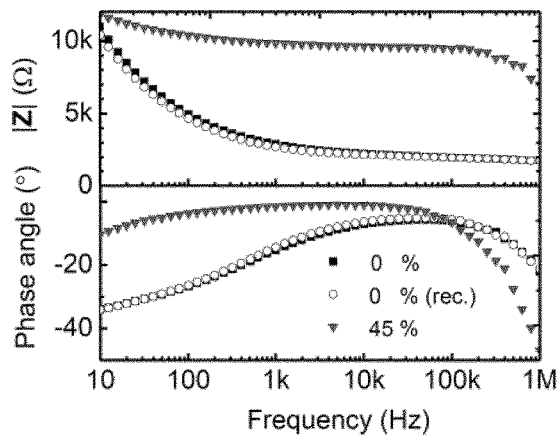
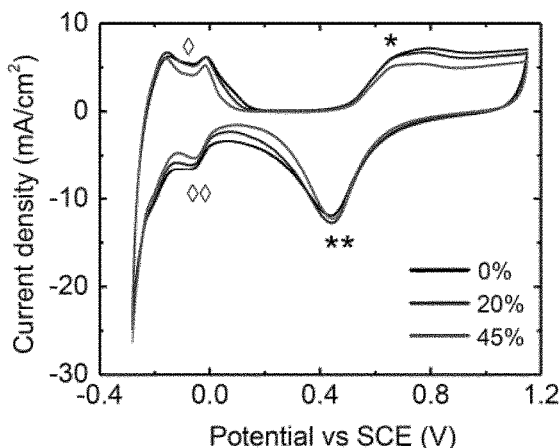
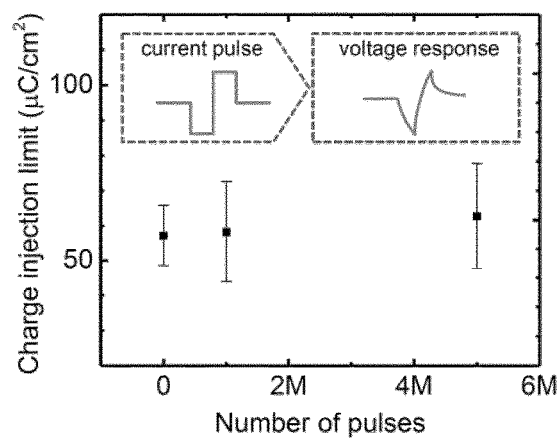
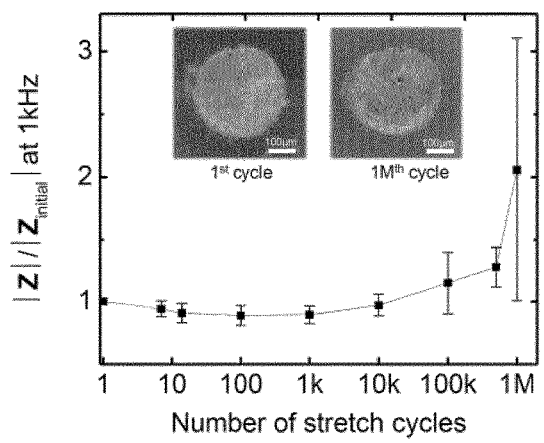
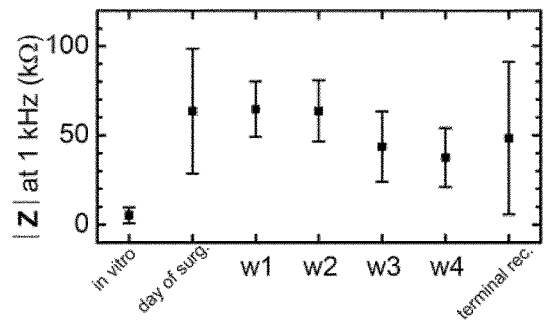
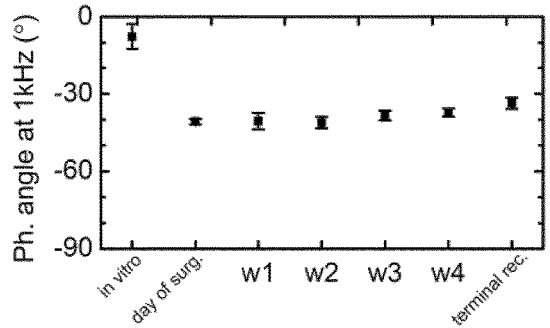

FIG. 23
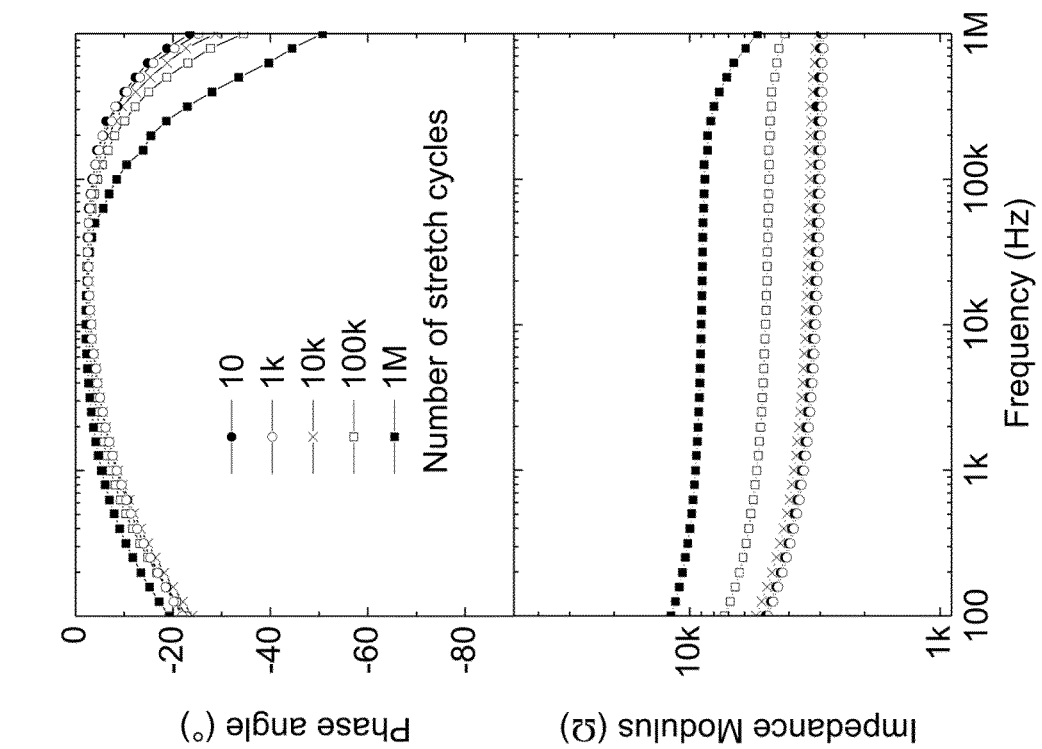
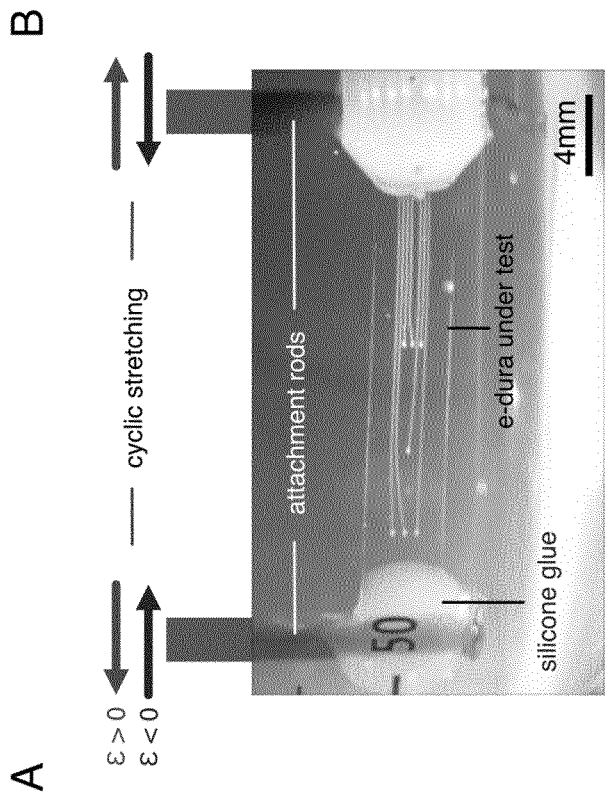

FIG. 27
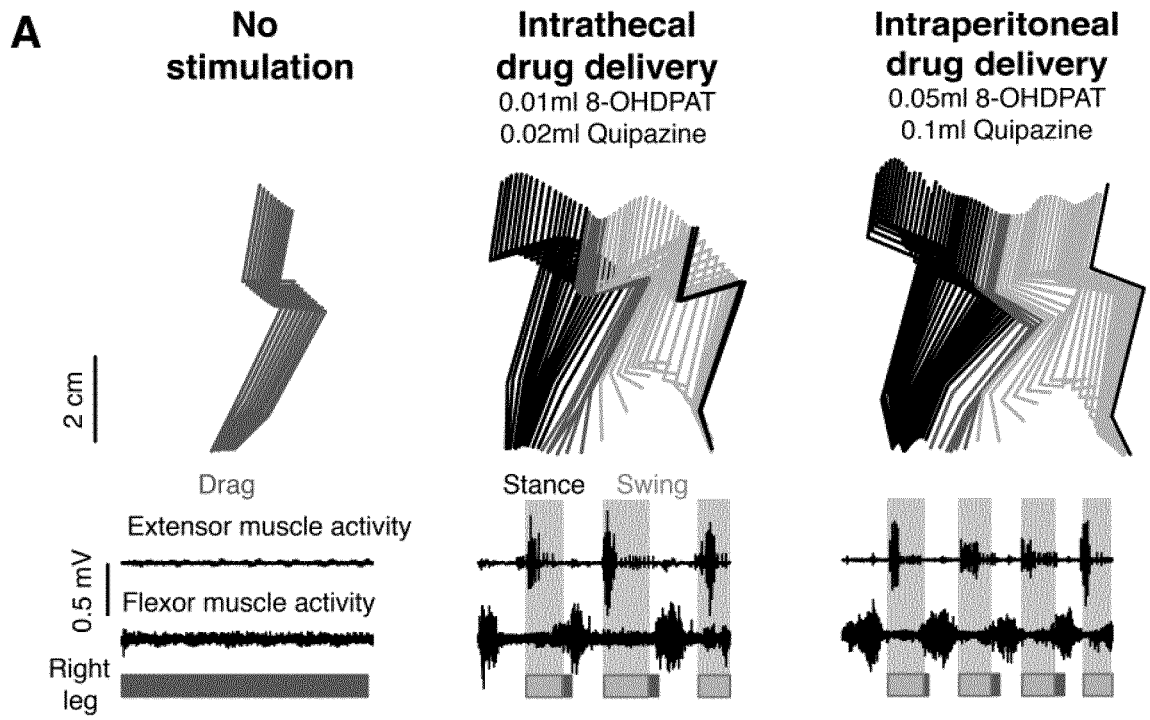
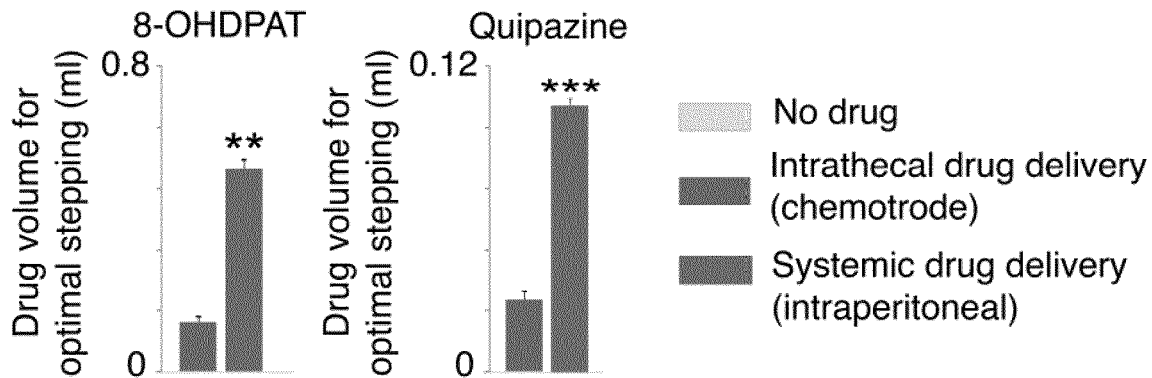
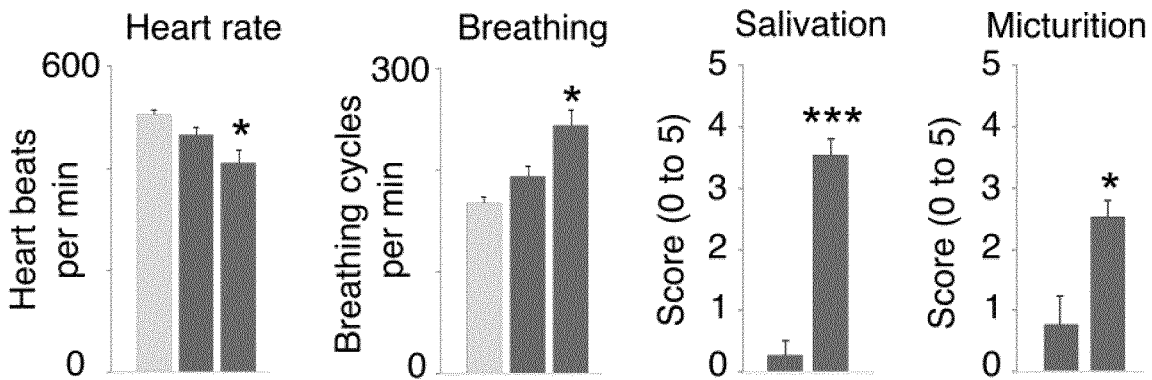

SYNTHETIC SKIN FOR RECORDING AND MODULATING PHYSIOLOGICAL ACTIVITIES

FIELD OF THE PRESENT INVENTION

The present invention relates to a device adapted to be implanted at the surface of electrically active biological tissues and organs for therapeutic and/or diagnostic purposes, and a method for producing same. In particular, the present invention relates to a device of the kind mentioned above, such device showing high till very high biointegration at the very surface of target human and/or animal organs. In more detail, the present invention relates to a multi-functional implantable device that possesses physical and/or mechanical properties mimicking the properties of biological membranes.

Within the meaning of the present invention "multi-functional" means, by way of examples, the ability to deliver electric impulses to biological tissues, and/or monitor electrical activity in biological tissues, and/or deliver light pulses and/or liquids to biological tissues, and/or extract liquids from cavities of the human body.

Still within the meaning of the present invention, "implantable" means the ability to conform to established and/or customised surgical procedures and to reside in vivo without producing adverse biological reactions over extended periods of time.

In the frame of the present invention, "physical and/or mechanical properties" means, by way of examples, stress-strain behaviour, elastic modulus, fracture strain, conformability to curvilinear surfaces, thickness, area and shape which have to be as similar as possible to those to be found in tissues of the human body.

Furthermore, and still within the meaning of the present invention, "mimicking the properties of biological membranes" means mimicking properties such as, by way of examples, strain, elastic modulus, breaking strain, conformability to curvilinear surfaces, thickness, area, ratio between thickness and planar dimensions, shape or the like of biological tissues. The present invention relates in particular to a method for fabricating stretchable electronic devices (for example stretchable electrode arrays) using soft (for instance conductive) materials or a combination of soft materials, a method for fabricating soft microfluidic delivery systems (channels) using, in particular integrating said stretchable electrode arrays, and to a method for electrically connecting said stretchable arrays to standard rigid electronic devices/hardware. The present invention further relates to a soft conductive material suitable for producing stretchable arrays, to a stretchable array produced using said material and to a microfluidic delivery system comprising said stretchable array, and to a soft electrical connector linking the stretchable array to standard electronic hardware.

PRIOR ART

Stretchable, implantable devices are becoming more and more popular and find convenient applications in the field of wearable ("on-body" and "on-organ") electronic devices, and/or implantable neuroprosthetic interface applications, and/or as electrode arrays for cell culture and tissue slice culture, and/or even for sensing robotic skins or the like. Stretchable, implantable devices according to the prior art usually comprise stretchable microelectrode arrays; in fact, the most important characteristic or feature of stretchable microelectrode arrays (for instance MEAs), relates to the fact that same can withstand mechanical deformations such as flexing, stretching, torsion or the like, without electrical failure or loss of their electrical features (in particular electrical conductivity and impedance). Accordingly, microelectrode arrays (for instance MEAs) are particularly suitable to be used as a neural interface with the central nervous system, i.e. the spinal cord, brain, or the peripheral nervous systems, i.e. the ganglia and nerves, or soft biological tissue, for instance for the purpose of stimulating and/or recording neurological or cardiac activity (both in vitro and in vivo), as well as for monitoring hippocampal electrical activity after traumatic brain injury or bladder afferent activity, or even for stimulating electrical potential of excitable cells or the like.

Stretchable microelectrodes are stretchable implantable devices for which it has in fact been verified that their electrical impedance stays low and stable during the deformation applied once or multiple times, including after repeated torsions, and therefore facilitate the recording of biological electrical signals and ensure efficient functional electrical stimulation. In particular, in both cases of in vitro and in vivo applications, stretchable arrays did not show any degradation of the implant electrical interface, after extensive mechanical manipulations in saline conditions (in vitro) and even after several months of implantation (in vivo).

Microelectrode arrays are usually fabricated by thermally evaporating a metal (gold—Au and/or Chromium (or Titanium)/Gold—Cr/Au or Ti/Au) thin film on a soft PDMS (polydimethylsiloxane silicone substrate, 120 μm thick) using a polyimide shadow mask. The PDMS layer is cured at 80° C. for at least 12 hours. The resulting interconnect tracks may be 50 μm wide, and mm to cm long, for instance. The electrodes at one end of the interconnect tracks may be 300 μm diameter. The connector pads on the other end of the interconnect tracks may have an area of 1 $mm^2$ or smaller to allow for easier hand wiring later in the process.

Once the electrode array has been encapsulated, i.e. passivated whilst leaving the electrodes and connector pads exposed through connecting vias, the connecting vias may be filled with a conductive material, thus creating connection points or spots to the biological tissue (electrode end) and the electrical connector (connector pads end).

The conductive materials used for fabricating stretchable arrays must meet several requirements, in particular both mechanical and electromechanical requirements.

In particular, a relevant challenge relating to stretchable electrodes to be used as wearable electrodes, and/or for implantable neuroprosthetic interface applications, and/or even as electrode arrays for cell culture and tissue slice culture, and/or even for sensing robotic skins or the like, relates to the fact that, for these kinds of applications, the stretchable electrode arrays (in these cases also referred to as "bio-electrodes"), must be made, at least in part, of a biocompatible material with good charge injection properties.

Moreover, as anticipated above, neuroprosthetic medicine is regarded as a promising science expected to improve the lives of countless individuals. For instance, cochlear implants may restore hearing in deaf children, deep brain stimulation alleviates Parkinsonian symptoms, and spinal cord neuromodulation attenuates chronic neuropathic pain. These interventions rely on implants developed in the 1980s. Since then, advances in electroceutical, pharmaceutical, and more recently optogenetic treatments triggered development of myriad neural interfaces that combine multiple modalities. However, the conversion of these sophisticated technologies into chronic implants mediating long-lasting functional benefits has yet to be achieved. For instance, a recurring challenge restricting chronic bio-integration is the substantial biomechanical mismatch between implants and neural tissues.

Moreover, a further drawback of implantable devices according to the prior art relates to the fact that same still do not adequately mime the physical, in particular mechanical properties of biological (human) tissues.

Accordingly, a further goal of the present invention is that of introducing a new class of soft multimodal neural interface devices allowing to mime the physical, in particular mechanical properties of biological membranes and/or tissues in general, thus achieving chronic bio-integration.

BRIEF DESCRIPTION OF THE PRESENT INVENTION

In the following, description will be given of examples according to which the methods according to the present invention are carried out for producing conductive materials, passivating, encapsulating and even producing and/or fabricating stretchable arrays, as well as for producing microfluidic delivery systems to be used as implantable devices mimicking biological membranes.

However, it has to be noted that the possible applications of the methods and materials according to the present invention are not limited to the case of stretchable microelectrode arrays and/or microfluidic delivery systems; to the contrary, the methods according to the present invention are adapted to be carried out and the materials according to the present invention are suitable to be used for producing or fabricating soft electrical and/or electronic circuits or optoelectronic circuits or conductive paths.

An embodiment of the present invention relates to a method for manufacturing a microelectrode array, forming at least one conductive path on a support, encapsulating said at least one conductive path by means of an encapsulation layer comprising at least one through via exposing at least one portion of said conductive path and filling said at least one via with a conductive material produced according to the method of the present invention.

Still according to the present invention, a new class of neural implants with the topology and compliance of dura mater, the protective membrane of the brain and spinal cord, is introduced. These neural interfaces, also referred to as "e-dura", achieve chronic bio-integration within the subdural and/or epidural space better than achieved with state-of-the-art neural implants where they conform to the statics and dynamics of neural tissue. e-dura according to the present invention embeds interconnects, electrodes and chemotrodes that sustain millions of mechanical stretch cycles, electrical stimulation pulses, and chemical injections. These integrated modalities enable multiple neuroprosthetic applications. e-dura extracted brain signals from the cortical surface of the brain in freely behaving animals for brain machine interface. Further, it is suitable for delivery of electrochemical spinal neuromodulation that restores locomotion after paralyzing spinal cord injury. e-dura according to the invention offers a novel platform for chronic multimodal neural interfaces in basic research, neuroprosthetic research and neuroprosthetic medicine.

Still according to the invention soft interfaces have been designed and engineered that mimic the topology and mechanical behaviour of the dura mater. The implants or interfaces may integrate a transparent silicone substrate (for instance 120 µm in thickness), stretchable gold or chromium/gold interconnects (for instance 35 nm in thickness), soft electrodes (for instance 300 µm in diameter) coated with platinum-silicone composite, and a compliant fluidic microchannel (for instance 100 µm×50 µm in cross-section). The interconnects and electrodes transmit electrical excitation and transfer electrophysiological signals. The microfluidic channel, also referred to as chemotrode, may be used to deliver drugs locally. Microcracks in the interconnects together with the newly developed soft platinum-silicone composite electrodes confer exceptional stretchability to the entire implant. The patterning techniques of metallization and microfluidics support rapid manufacturing of customized neuroprostheses.

Still according to the invention a soft electrical connector has been designed and engineered to enable a precise, reliable and robust electromechanical coupling with the soft array and standard electronic hardware.

The compliance of e-dura enables chronic implantation below the dura mater without extensive durotomy. This location provides an intimate interface between electrodes and targeted neural tissues, and allows direct delivery of drugs into the intrathecal space.

Further embodiments of the present invention are defined in the appended claims.

BRIEF DESCRIPTION OF THE DRAWINGS

In the following, description will be given of the embodiments of the present invention depicted in the drawings. It has however to be noted that the present invention is not limited to the embodiments depicted in the drawings and described below; to the contrary, the present invention comprises all those embodiments which fall within the scope of the appended claims.

In the drawings:

FIGS. 1a to 1b, 2a to 2c, 3a to 3b, 4a to 4b and 5a to 5b depict method steps of a method according to an embodiment of the present invention;

FIGS. 9, 10(a) and 10(b) depict method steps of a method according to a further embodiment of the present invention;

FIGS. 11 and 12 show examples of implantable devices according to the present invention.

FIGS. 13 to 28 relate to examples of checks and studies carried out in the frame of the present invention.

DETAILED DESCRIPTION OF THE PRESENT INVENTION

Figure 1A:
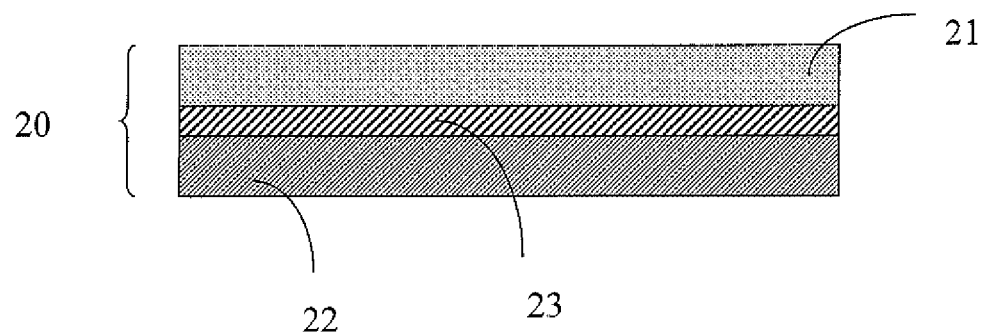

In FIGS. 1 to 5, the reference 10 identifies an electrode array, for instance a microelectrode array comprising at least one conductive path; in the following, for the sake of convenience and clarity, the electrode array 10 will be eventually simply referred to as a "conductive path" or "array of conductive paths". Said conductive paths 10 may be formed according to any of the methods known in the art such as, for instance, deposition of a continuous metal film and etching, metal evaporation or the like. Since the particular method used for forming the conductive path 10 does not fall within the scope of the present invention, detailed description of same is omitted for the sake of conciseness.

The thickness of the layer 21 carrying the 'array of conductive paths' is determined by the application requirements (i.e. to impart tensile properties of the functional device similar to biological membranes as measured in stress-strain extensiometry tests and known in the literature) with thickness limitations of known methods for depositing such layers. By way of example for silicone rubber, the thickness of the layer can vary between 1 μm to 10 mm.

The conductive paths 10 are formed on a support carrier 20 comprising, in addition to the layer 21, a rigid support or layer 22, for instance a silicon wafer 22. The soft and/or rubber layer 21, for instance a polydimethylsiloxane (PDMS) layer of a predefined thickness (for instance, about 100 μm but can vary between 1 μm to 10 mm). As further possible materials soft or flexible polymers such as silicones, polyurethanes, polyimide, parylene may be cited. As a rigid inorganic material, silicon or glass, by way of example, may be used. It has moreover to be noted that the thickness of the layer carrying the 'array(s) of conductive paths' is determined, as anticipated above, by the application requirements. By way of example, for silicone rubber, the thickness of the layer 21 can vary from 1 μm to 10 mm.

Still by way of example, the layer 21 may be spin coated on the rigid support 22 and cured, with excess PDMS material cut around the wafer.

Eventually, for purposes which will become more apparent with the following description, a release layer 23 may be formed between the rigid support 22 and the PDMS layer 21 to allow or at least facilitate late removal of the rigid support (silicon wafer) 22. By way of example, the release layer may comprise a water soluble layer such as spin coated Polyvinyl alcohol or polystyrene-sulphonic acid, or a self-assembled monolayer such as formed by 1H, 1H, 2H, 2H-Perfluorooctyltriethoxysilane, or trimethylchlorosilane, or UV sensitive adhesive.

In the following, a first embodiment of a method according to the present invention will be described with references to FIGS. 2 to 5, wherein corresponding features are identified by corresponding reference numerals.

As depicted in FIGS. 2 to 5, a double passivation layer is used, namely a passivation layer 1 comprising first and second passivation sub layers 1a and 1b, wherein by means of said first and second passivation layers a further step can be carried out in the process chain for producing conductive paths or microelectrode arrays, in particular stretchable microelectrode arrays, for instance MEAs (gold microelectrode arrays).

As stated above, by way of example, the microelectrode array 10 may be fabricated by thermally evaporating a metal (Au or Cr/Au or Ti/Au or Cr/Au/Cr or Ti/Au/Ti) thin film on a soft PDMS (polydimethylsiloxane silicone substrate 21, 120 μm thick) using a shadow mask. The PDMS layer may be cured at 80° C. for a predefined time. The resulting interconnects may be 100 μm wide, and 13.5 mm long, for instance. The connector pads may have an area of 1 mm$^2$ each to allow for easier wiring later in the process. The conductive paths 10 may be composed of Ti/Au/Ti layers that are 5/30/3 nm thick, respectively, with the Ti layers used to improve adhesion.

Figure 1B:
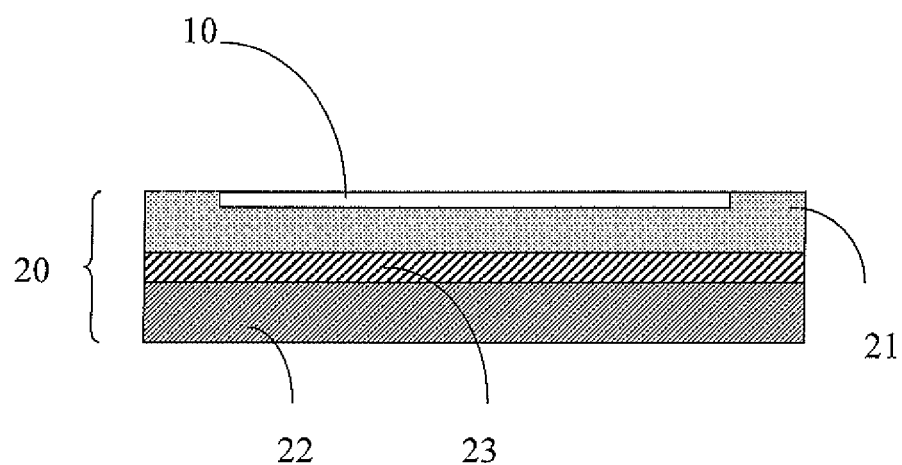
Figure 2A:
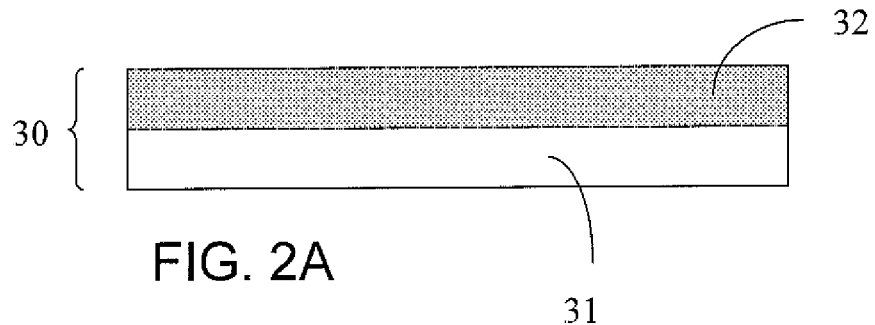
Figure 2B:
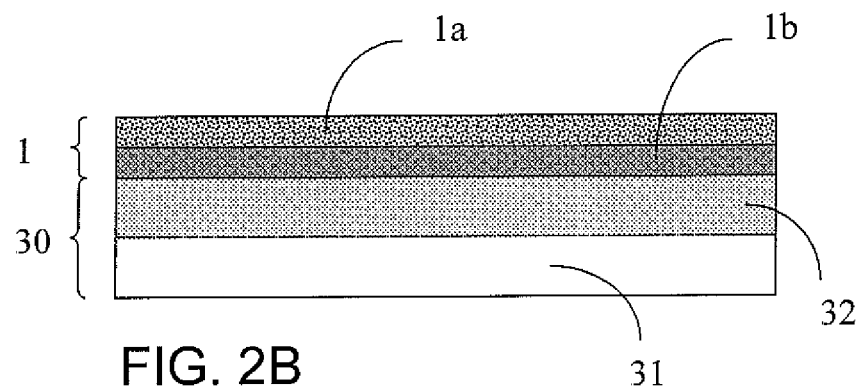
Figure 2C:
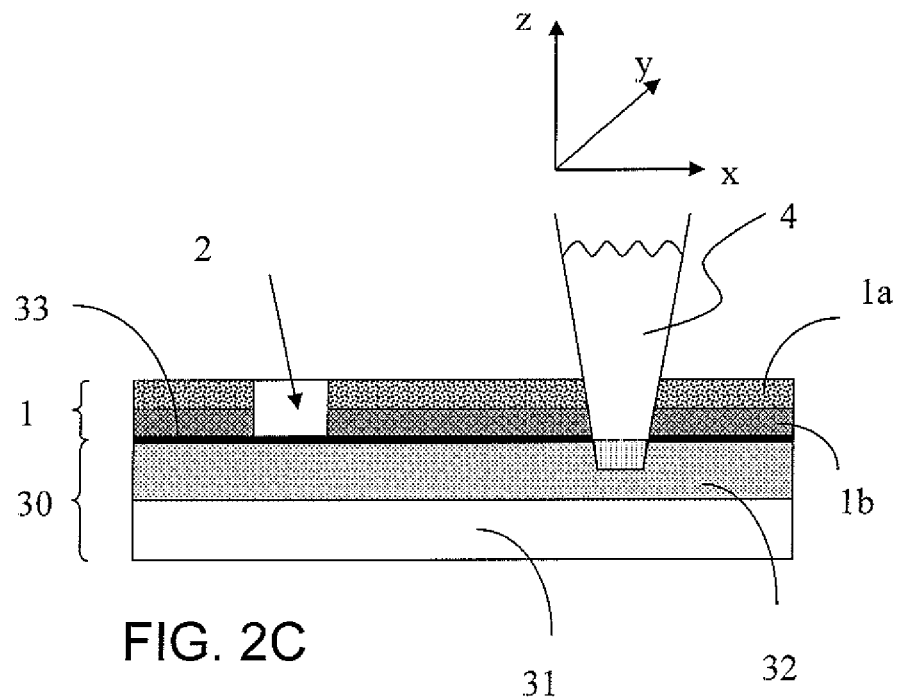

At the stage depicted in FIGS. 1a and 1b, namely with an array of conductive paths 10 formed on a stack comprising a rigid support 22 (for instance a silicon wafer), a soft or rubber layer 21 (for instance a PDMS layer) and eventually a release layer 23 therebetween, the method is prosecuted as depicted in FIGS. 2a to 2c.

As depicted in FIGS. 2a to 2c, according to the embodiment, a substrate 30 is provided, wherein said substrate 30 may comprise, as depicted, a transparent carrier 31, for instance a glass slice or wafer, wherein the substrate 30 may comprise a further layer 32, for instance a soft or rubber PDMS layer. For instance, said layer 32 may be spin coated or drop casted on the carrier 31 and cured, with the excess PDMS material cut around the carrier 31, wherein the soft or rubber layer 32 facilitates the formation of through vias in a passivation layer to be deposited on said layer 32. However, within the scope of the present invention, the layer 32 may be made of transparent silicone rubber such as PDMS. By way of example the thickness of this layer may range from 4 to 10 mm.

As depicted in particular in FIG. 2b, a passivation or encapsulating layer 1 is formed on the layer 32, wherein however, in this case, the passivation layer 1 comprises a first passivation layer 1b and a second passivation layer 1a; again, each of said first and second passivation layers 1b, 1a may be a silicone layer spin coated on the layer 32 and cured. In particular, in the case of silicone rubber the convenient thicknesses for layers 1a and 1b may range from 1 μm to 1 mm. Alternatively, other elastomers can be used such as, for example, polyurethane or the like. An alternative method to form layer 1 is lamination.

Moreover, for allowing later removal of one or both of the layers 32 and 1b, non-stick release layers (one non stick release layer 33 being depicted) may be formed between the layers 32 and 1b, as well as between the encapsulation layers 1a and 1b, respectively; for instance, to this end, the upper surface of each of the layers 32 and 1b may be coated with a release layer such as that formed by a self-assembled monolayer of 1H, 1H, 2H, 2H-Perfluorooctyltriethoxysilane or trimethylchlorosilane molecules, or UV sensitive adhesives.

Moreover, according to a further step of the method according to the embodiment of the present invention as depicted in FIG. 3c, through vias 2 (at least one) are formed in the encapsulation layer 1, meaning through the encapsulation layers 1a and 1b. Within the meaning of the present invention, the expression "through vias" has to be understood as meaning through holes, meaning that at least a portion of the upper surface of the underlying layer 32 is exposed and no rests or residues of said layers 1a and 1b are left inside the vias 2.

Within the scope of the present invention, the vias 2 may be formed according to any convenient solution, in particular, as depicted, using a simple punching tool (essentially a hollow needle) 4, wherein the inside of the needle or puncher 4 may be filled with a small amount of liquid to aid the removal of the encapsulation material 1 (1a and 1b).

The shape and dimension (diameter or the like) of the vias 2 will correspond to those of the punching tool 4, wherein vias of different shape and/or dimension may be formed by using corresponding different tools.

Alternatively, vias may also be formed by etching methods through an etchant resistant (shadow) mask containing vias of different shapes. Etching methods may involve rotational drilling, milling, particle assisted abrasion, laser micromachining, plasmas or reactive gasses.

The layer 32 not only facilitates the handling of the encapsulation layer 1 (see below), but also facilitates the formation of the vias 2, in particular in the special case in which same are formed by means of a punching tool 4 as depicted. In fact the layer 32 facilitates the puncher 4 to be inserted even beyond the encapsulation layers 1a and 1b, meaning that the puncher 4 may be inserted to a depth which may be more than the thickness of the encapsulation layers 1a and 1b.

Figure 4A:
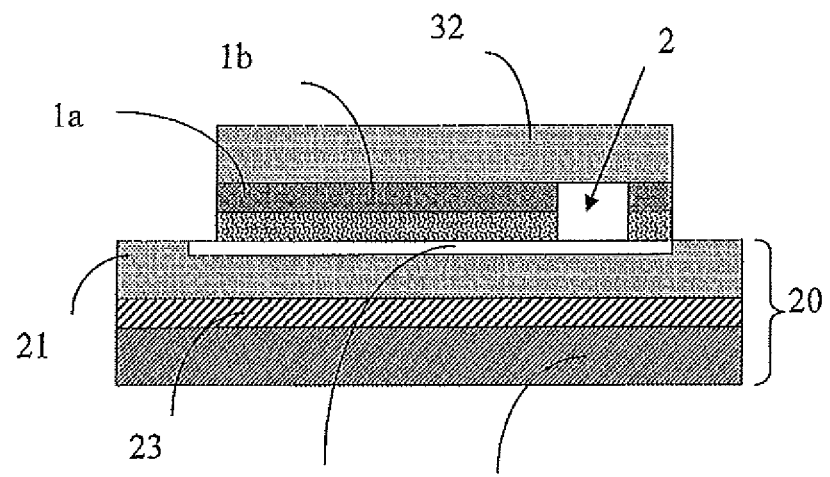
Figure 4B:
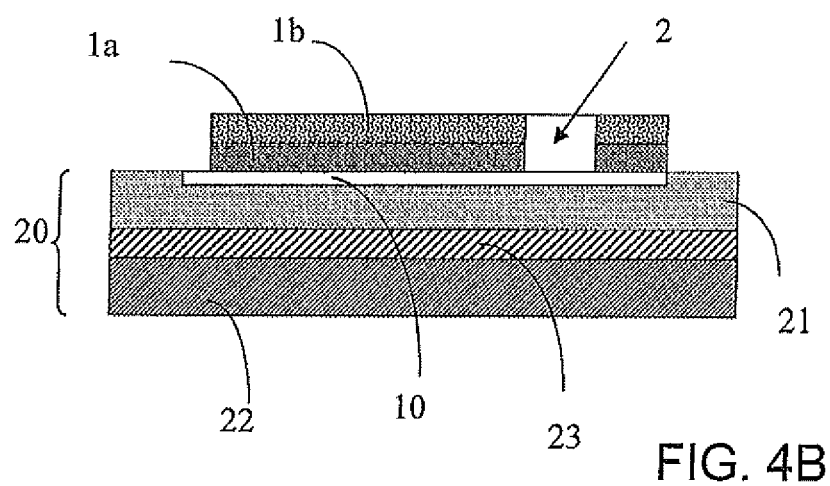

The method according to this embodiment of the present invention is prosecuted by carrying out the method steps depicted in FIGS. 3a, 3b and 4a, these steps comprising in particular:

inverting (flipping upside down) the stack comprising the layers 31 if any), 32, 33 (if any) and 1 and aligning the vias 2 with predefined portions of the conductive paths 10, for instance those portions to be used as contact pads (FIG. 3a);

bringing into contact the passivation layer 1 with the support carrier 20, meaning bringing the passivation layer 1a into contact with the conductive paths 10 and/or layer 21 and bonding the passivation layer 1a and the layer 21 (FIG. 3b);

removing the carrier and/or support layers (the rigid and/or transparent carrier 31 and/or the soft or rubber layer 32 (if any).

The resulting structure will therefore comprise (see FIG. 4b) conductive paths 10 duly passivated by the passivation layers 1a and 1b (with vias 2).

The method is then prosecuted by carrying out the further steps of same as depicted in FIGS. 5a and 5b.

In particular, as depicted in FIG. 5a, the vias are filled with conductive material 50.

Finally, during a further step as depicted in FIG. 5b, the first encapsulation layer 1b is peeled off from the second encapsulation layer 1a, thus removing also excess of conductive material 50 eventually lying on the layer 1b outside the vias.

The resulting structure is therefore a duly passivated array of conductive paths 10, eventually formed on a stretchable layer, wherein the contacting vias 2 are already filled with conductive material 50.

A method having been described for manufacturing electrode arrays, said method comprising in particular filling the vias with a conductive material, description will be given in the following of a further method according to the present invention by means of which a convenient conductive material is produced, said conductive material allowing easy filling of the vias and showing improved mechanical and electromechanical characteristics (such as improved stretchability, biocompatibility, improved electrical conductivity, improved charge injection properties or the like), The conductive material or composite prepared according to the following description is a blend of platinum nano-micro particles and PDMS silicone.

According to the method, a PDMS pre-polymer (for instance composed of organosilicon monomers or oligomers which are capable of further reactions to form high molecular weight polymers) is mixed with its cross-linker. In its pre-polymer form PDMS has the consistency of honey, flows easily (5000 cP) and is stable. The cross-linker initiates the polymerization reaction, which transforms the oligomers into high molecular weight chains of polydimethylsiloxane. When the curing reaction is completed (usually several hours later), the result is the elastomer.

As an example, both pre-polymer and cross-linker may be of the kind as supplied by the manufacturer (e.g. Dow Corning). In particular, a possible ratio of the products used may be 10:1 prepolymer:crosslinker. However, within the frame of the present invention, other similar two component elastomer kits are possible, for example based on polyurethanes, even if their high viscosity (1000 s cP) prior to curing makes mixing with the metallic micro particles more difficult.

Moreover, once mixed with its cross-linker, the PDMS is diluted in heptane (or another low molecular weight alkane such as hexane) in a 1:2 w:w ratio, until a low viscosity liquid is obtained. It has however to be noted that different ratios are also possible, as long as 1:>2 (for example 1:3); adding more heptane lowers the viscosity, more time being needed for its evaporation, accordingly.

The procedure is then prosecuted by adding 100 mg of platinum microparticles to 5 mg of the PDMS based low viscosity liquid (or, in other words, to 15 μL of the heptane diluted PDMS). In particular, platinum powder with particles size between 0.5 μm and 10 μm may be conveniently used.

The mixture is then thoroughly stirred (for instance by hand for approximately. a minute long using a cocktail stick) and put aside for evaporation of the heptane fraction (for instance until Ideally no heptane is left).

As an example, for the purpose of evaporating the heptane fraction, the mixture may be left at room temperature (for approximately 10 minutes) to avoid the PDMS starting to cross-link. However, using an oven at a predefined temperature higher than the room temperature also falls within the scope of the present invention as well as putting the mixture in a chamber under mild vacuum to aid the evaporation of the solvent.

The addition of 5 mg amounts (also referred to as singular doses) of PDMS is repeated (on average four times, wherein after each addition, evaporation of the heptane fraction is allowed (see as described above).

No further PDMS is added once the mixture becomes a paste, wherein paste formation occurs once the PDMS content corresponds to 15-20% by weight and the heptane has substantially or fully evaporated.

The conductive paste obtained according to the above described method revealed to be particularly useful for filling conductive vias, for instance as described with reference to FIGS. 5A and 5B. In particular, the paste showed improved filling properties, along with excellent stretchability and charge injection. It has however to be noted that the paste allows the vias to be filled in a very simple way, for instance by spreading and pressing the paste, even manually, on the encapsulation layer 1b wherein, eventually and according to the needs and/or circumstances, the paste may be temporarily thinned with a drop of pure heptane, wherein the amount of heptane to be used depends on the amount of paste to be diluted or used. As an example, for the whole 100 mg of Pt, 10-20 μl of pure heptane. may be used.

After deposition of the paste, the (silicone fraction of the) paste is allowed to polymerise at room temperature for 48 hours or for a shorter time at elevated temperature inside an oven (for example 80° C. for 2 hours)

Whilst in the embodiment of the method as described above micro-nano particles of platinum are used, it has to be noted that using micro-nano particles of one or more of platinum, iridium, iridium oxide and similar metals and/or metal oxides also falls within the scope of the present invention.

Figure 6:
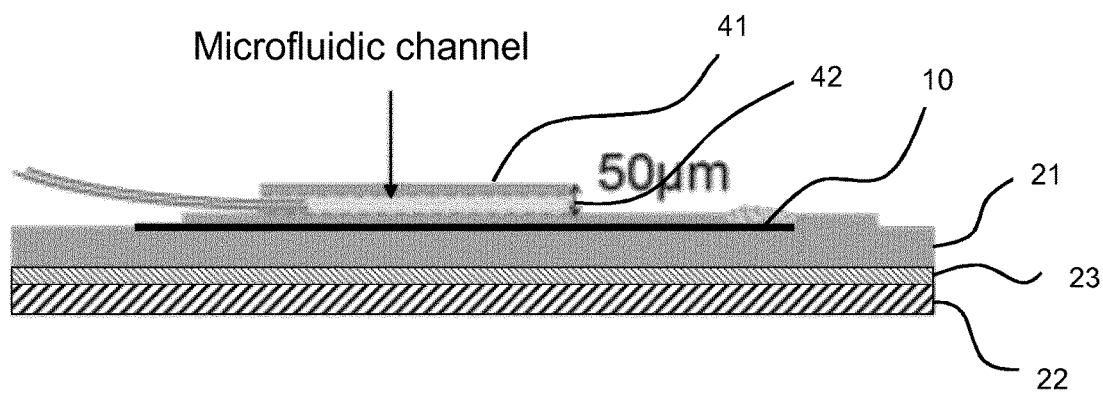
FIGS. 6 to 8 and 8(a) depict method steps of a method according to a further embodiment of the present invention.
Figure 7:
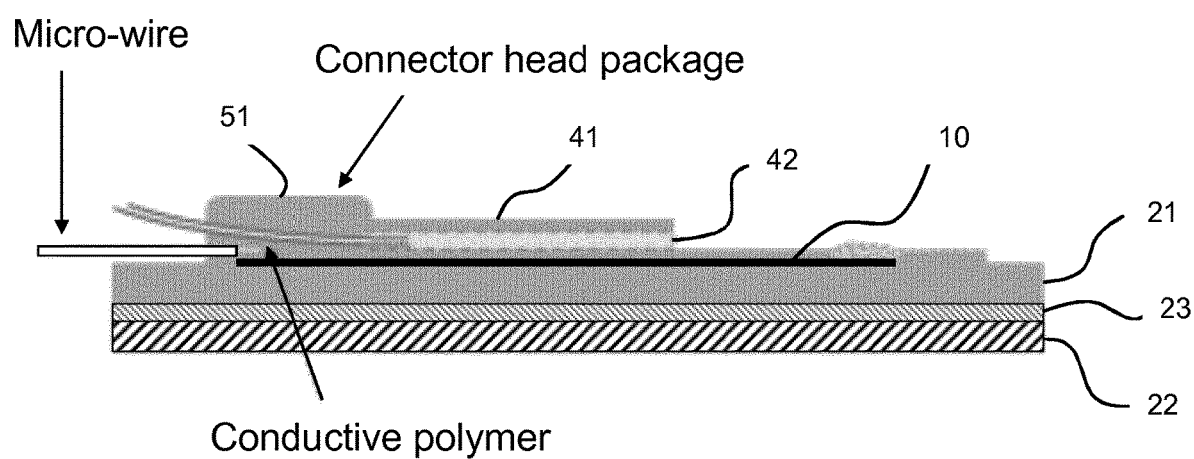
Figure 8:
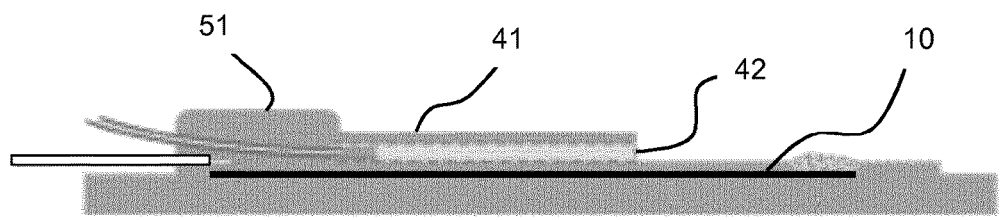

In the following, a method according to a further embodiment of the present invention for fabricating a microfluidic delivery system will be described with reference to FIGS. 6 to 8.

To form the microfluidic delivery system, an additional 80 μm thick PDMS layer 41 is bonded to the metallized and electrically passivated e-dura substrate comprising the rubber layer 21 and conductive paths 10 thereon. This layer 41 contains at least one microfluidic channel 42 (100×50 μm2 in cross section), terminating at a pre-determined position on the e-dura substrate (e.g. in the vicinity of an electrode).

Figure 8A:
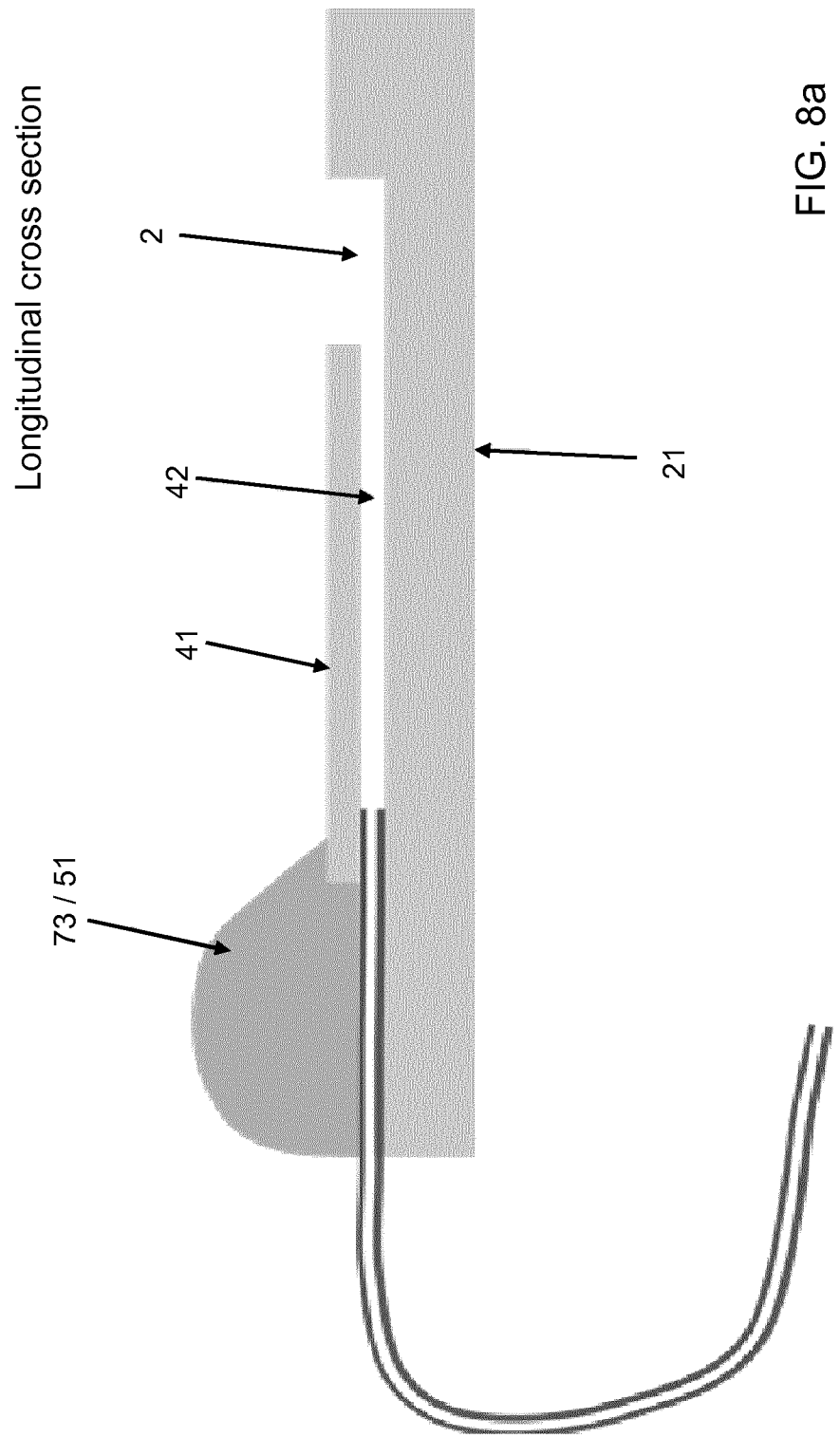

As an example, as depicted in FIG. 8a, the at least one microchannel 42 can be formed in the layer 41 prior to bonding to substrate 21. Such microchannel may be formed by etching methods of the kind described above. The microchannel may terminate into the side wall of one of the vias 2 (see the above description) thus forming an outlet/inlet for the fluid.

The connector side of the microchannel 42 is interfaced with a flexible polyethylene capillary (for instance 0.008" i.d., 0.014" o.d., Strategic Applications Inc.) and sealed with a bolus of silicone 73 or 51 (for instance KWIK-SIL, World Precision Instruments).

In the following, with reference to FIG. 9, a method according to a further embodiment of the present invention for integrating and mounting rigid electronic components onboard the stretchable, implantable device is disclosed.

The method enables the establishment of an electrical connection between the stretchable conductive paths 10 of the stretchable array and standard, rigid/flexible printed circuit boards, packaged chips or bare chip dies or the like.

As apparent from the drawings, starting from a stretchable substrate 21 (for instance a PDMS substrate) with stretchable conductive paths 10 on a surface thereof (see for instance the disclosure relating to FIGS. 1 to 5), the connection is established by depositing small boluses 70 of a soft and conductive material, for instance a paste or a composite, onto pre-defined areas of the stretchable conducting paths of the stretchable array. By way of example, the predefined areas may correspond to the vias 2 formed in the passivation layer 1 (see FIG. 4b and the corresponding disclosure). Still by way of example, the soft and conductive material of the boluses 70 may be the same filler conductive material 50 as described above with reference to FIG. 5a; however, according to the needs and/or circumstances, the two materials 50 and 70 may be different. Deposition of the soft and conductive material 70 may be done, for instance, by screen printing through a mask, extrusion through a nozzle, evaporation through a mask or manual placement using a cocktail stick. The boluses 70 of paste or conductive material may have spherical shape with diameters ranging from 5 μm to 5 cm. The paste may be a composite of conductive metallic particles dispersed in a polymeric binder.

The tips or pins or pads 71 of, for instance, electrical wires, rigid connectors, chips, PCBs, dies or the like are then inserted or placed on the conductive paste using manual alignment or an alignment tool potentially using a microscope aid. The resulting assembly therefore may consist of at least one pin, of a wire, PCB, chip, die 72 or the like or a combination thereof. As a non limiting example, the resulting assembly may consist of an array of wires/pins held together on a PCB, chip or wires aligned in a clamp.

Following placement of the wire/s (pin/s) in the conductive paste or material 70, the surroundings of the connector (at least those of the wire or PCB or chip or die 72) are flooded with a viscous silicone elastomer 73 or a similar electrically insulating polymer. Following curing of the connector package, the silicone elastomer 73 polymerises to form an electrically insulating package that mechanically stabilises the connector and immobilises the wires/pins 71 onto the stretchable electrode array 10 and prevents the conductive paste or material 70 inside from flowing out of the connector or shorting the pins/wires 71. The conductive paste or material 70 inside the connector remains soft and/or viscous after the curing of the outer silicone packaging. It serves as a mechanical buffer between the stretchable metallisation 10 of the array and the rigid (non-stretchable) wires/pins/PCB contacts. Therefore the presence of the soft paste or material prevents stress concentration to occur at the soft-rigid boundary and thus prevents the damage and/or destruction of the stretchable conductive elements when the device is stretched.

In the following, with reference to FIGS. 10(a) and 10(b), methods according to corresponding further embodiments of the present invention for connecting a stretchable, implantable device to, for instance, external electronic devices such as an electrical cable, a battery or telemetry unit or the like are disclosed, wherein the electrical cable or the battery or telemetry unit or the like may also be implanted in the body.

Figure 10A:
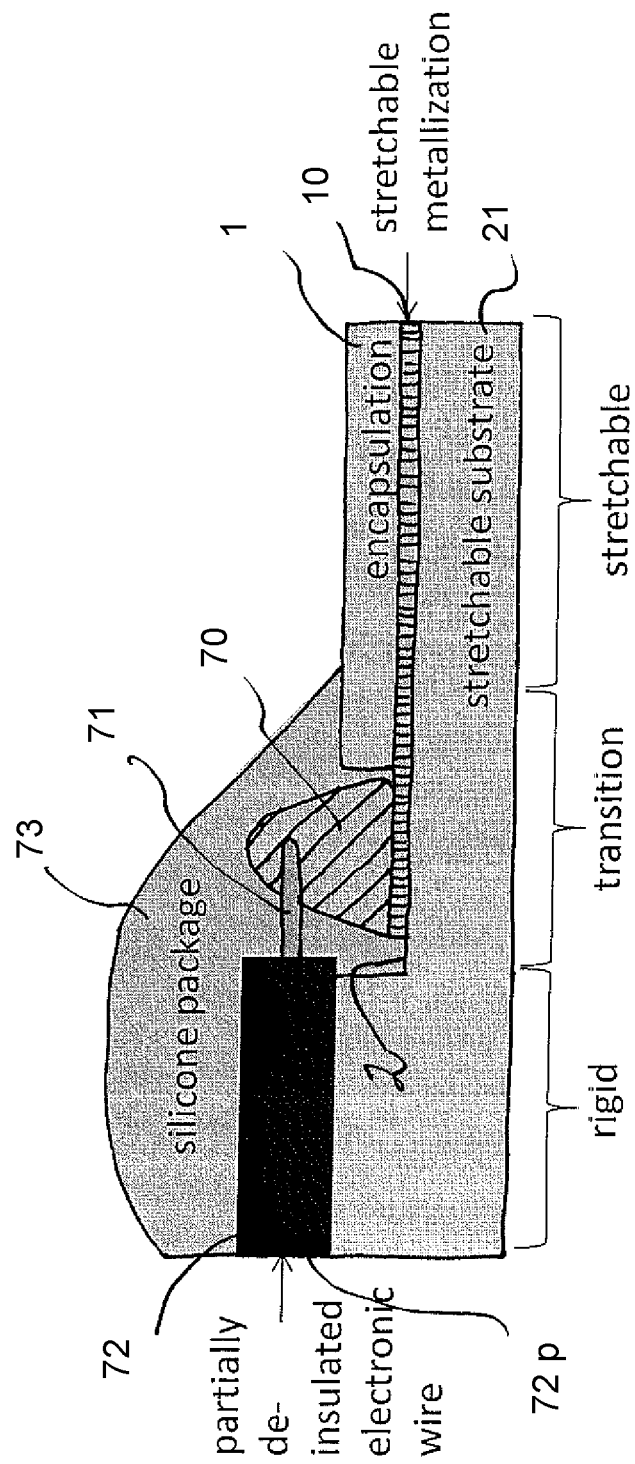

FIG. 10(a) shows a longitudinal section of the implantable device of FIG. 9; as depicted in FIG. 10(a), a portion 72p of the wire, PCB, chip, die or the like 72 may be left exposed, for instance by cutting off the elastomer 73; the exposed portion may comprise, for instance, contact pads, electrodes or the like. This solution allows the soft device to be implanted into the human body, for instance for the purpose of monitoring electrical activity of the brain or the like, or even for stimulating electrical activity.

Alternatively, as depicted in FIG. 10(b) (which shows a longitudinal section of the electrical connector), a portion 74p of at least one wire 74 may be left exposed for instance by stripping off its insulation. The at least one exposed portion 74p of the wire 74 is placed inside soft conductive paste or material 70. In both cases of FIGS. 10(a) and 10(b), following connection of the wire 74, 72 (or PCB, chip, die or the like) with the conductive paste or material 70, the surroundings of the connector are flooded with a viscous silicone elastomer 73 or a similar insulating polymer. Following curing of the connector package, the silicone elastomer 73 polymerises to form an electrically insulating package that mechanically stabilises the connector and immobilises the wire 74, 72 onto the stretchable electrode array 10 and prevents the conductive paste or material 70 inside from flowing out of the connector or shorting the wire 74, 72.

FIGS. 11(1) to 11(7) show top views of examples of implantable devices according to the present invention; FIGS. 12(1) to 12(5) show cross sectional views of some of the devices according to FIGS. 11(1) to 11(7). Moreover, in FIGS. 11(1) to 11(7) and 12(1) to 12(5) letters (b) to (f) indicate the corresponding positions of the cross sections along the devices.

FIG. 11(1) shows a top view of the device according to FIGS. 9 and 10.

As depicted in FIGS. 11(1) and 9 and 12(5), the device may comprise an optoelectronic component, for instance a light emitting diode or a photodiode.

As depicted in FIGS. 11(2) and 12(2), the device may comprise a waveguide 80.

As depicted in FIGS. 11(3) and 12(1), the device may comprise a cavity 81, said device being therefore suitable for delivering and/or collecting fluids.

As depicted in FIGS. 11(4), 12(3) and 12(4), the device may comprise conductive paths, microelectrode arrays or the like 10 and eventually vias filled with a conductive paste 50.

The device according to FIG. 12(5) corresponds to that according to FIG. 9.

Moreover, as depicted in FIGS. 11(6) and 11(7) and 12(5) the device may comprise one or more sensors (for instance temperature sensors) and/or one or more transistors.

Further Studies, Checks and Results

For the purpose of the biocompatibility study, soft e-dura implants according to the present invention and stiff implants were designed and fabricated. Four copies of each type were fabricated and implanted chronically in the subdural space of the lumbosacral spinal cord in healthy rats. The purpose of the study is to demonstrate that functional (electrical/fluidic) e-dura implants that mimic the mechanical properties of natural dura mater exhibit better biocompatibility than stiff implants that do not. The ability to mimic the mechanical properties of dura mater are enabled by the process and materials choices described above.

e-dura Implants

The e-dura were functional silicone implants, including both the microfluidic channel and seven electrodes, and were designed to fit the intrathecal space of the spinal cord. The implants were prepared following the process presented above.

Stiff Implants

Stiff implants were cut out from 25 µm thick polyimide foil (Kapton™-100 HN, DuPont). The intraspinal dwelling portion of these devices was 3.2 mm wide and 3 cm long. The contour of the implant was cut out using a laser micromachining tool (LAB 3550, Inno6 Inc.) and had rounded edges to minimize tissue trauma during insertion. At its caudal end, the implant integrated the same transspinal electrical connector as the one used in the soft implants. However, neither electrodes nor interconnects were patterned on the polyimide foil. The dummy connector was 8 mm long, 11 mm wide and 2 mm thick and coupled seven insulated wires (multistranded steel insulated wire, 300 µm o.d., Cooner wire Inc.) that run sub-cutaneous away from the spinal orthosis to a head mounted socket (12 pin male micro-circular connector, Omnetics corp.).

Sham-Operated Rats

Sham-operated rats received an implant without intraspinal portion. The implant consisted of the same connector as that used in the other two types of implants, which was secured with the spinal orthosis, and then attached to seven wires running subcutaneously, and terminating in a head-mounted Omnetics connector.

In vitro electrochemical characterization of e-dura electrodes according to the present invention to check that the functionality (electrical/fluidic) of e-dura is maintained when it experiences mechanical deformations similar to those experienced by real dura in vivo.

In vitro Electrochemical Impedance Spectroscopy of e-dura Electrodes According to the Present Invention under Stretch (FIG. 15A,15E, FIG. 23)

An experimental set-up was developed combining electrochemical impedance spectroscopy with cyclic mechanical loading. The e-dura implant under test was mounted in a customized uni-axial stretcher and immersed in saline solution to conduct electrochemical characterization of the electrodes following different stretching protocols.

Electrochemical Impedance Spectroscopy measurements were conducted in phosphate buffered saline (PBS, pH 7.4, Gibco) at room temperature using a three-electrode setup and a potentiostat equipped with a frequency response analyzer (Reference 600, Gamry Instruments). A 5 cm long Pt wire served as counter electrode and a Standard Calomel Electrode (SCE) as reference. Impedance spectra were taken at the open circuit potential. The excitation voltage amplitude was 7 mV. Impedance spectra of individual electrodes were measured at tensile strains of 0%, 20% and 45%.

Stretching in PBS of the e-dura implants was conducted in a LabView-controlled, custom-built uniaxial tensile stretcher programmed to actuate two clamps moving in opposite directions along a horizontal rail. Each clamp held a stiff plastic rod pointing downwards from the plane of motion. The lower halves of the rods were submerged in a vessel holding electrolyte. The device under test was attached to the submerged part of the rods with silicone glue (KWIK-SIL, World Precision Instruments), so that the motion of the clams was transferred to the device under test. The stretcher was programmed to hold the implant under test at a specific strain or to execute a pre-set number of stretch-relaxation cycles (for example 0%-20%-0% at a stretch rate of 40%/s).

Cyclic Voltammetry (CV) of Electrodes under Stretch (FIG. 15B)

CV responses were recorded in 0.15 M $H_2SO_4$ (pH 0.9) under $N_2$ purge. A potential scan rate of 50 mV/s was used within the potential range of −0.28V to +1.15V (vs. SCE). Due to the difference in pH, this potential range corresponds to −0.6V to +0.8V (vs. SCE) in PBS. For each tested electrode, 20 priming cycles (1,000 mV/s) were applied to allow the electrode to reach a steady state.

Figure 22:
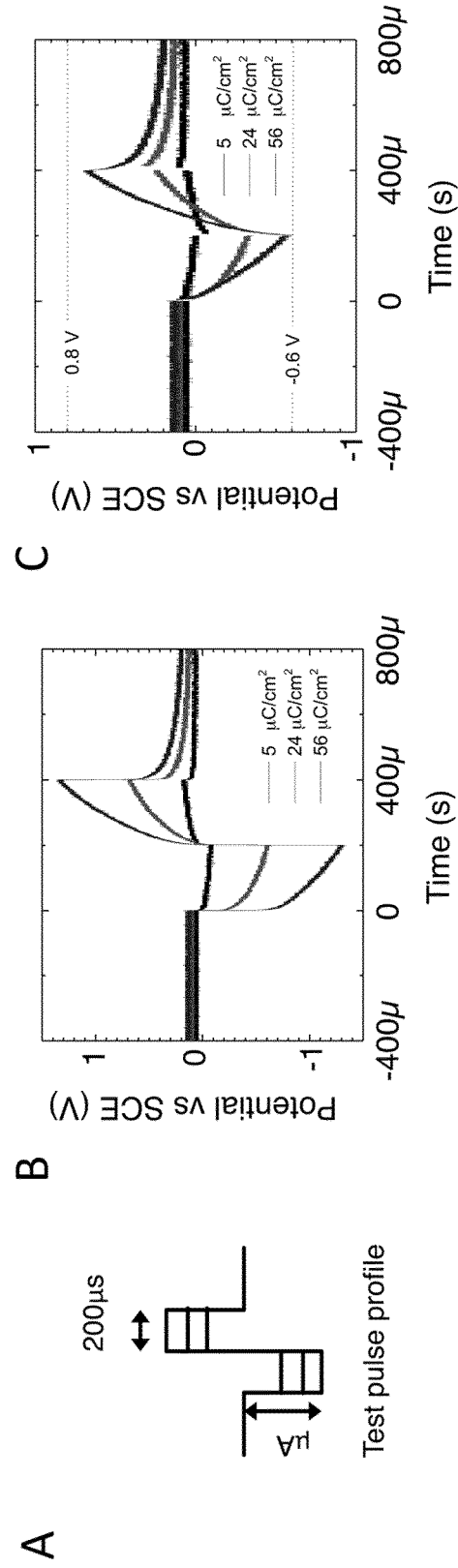

Charge Injection Capacity (CIC) of e-dura Electrodes According to the Present Invention (FIG. 22, FIGS. 15B and 15C)

CIC is a measure of the maximum charge per phase per unit area an electrode coating can deliver through reversible surface reactions. For CIC determination, electrodes with the platinum-silicone composite coating were immersed in PBS and cathodic-first, biphasic current pulses (200 µs per phase) were passed between the electrode and a large platinum counter electrode. A pulse stimulator (Model 2100, A-M Systems) delivered the current pulses, and the electrode polarization (vs. SCE) was recorded on an oscilloscope (DPO 2024 Digital Phosphor Oscilloscope, Tektronix). The amplitude of the current pulses was gradually increased until the electrode under test was polarized just outside the water window (the instantaneous polarization of the electrodes due to Ohmic resistances in the circuit was subtracted from voltage traces).

For experiments where the CIC was determined after cyclic pulse delivery, the repeating pulses were charge balanced, biphasic (200 µs per phase) with amplitude of 100 µA.

Tensile Mechanical Properties of Rat Spinal Cord (FIG. 13B)

A section of rat dura mater was explanted from a 2-month old Lewis rat and cut to a strip with dimensions of 3.4 mm×1 mm. Immediately post explantation, each end of the strip was secured to a glass cover slip using a fast acting cyanoacrylate adhesive. The cover slips were inserted into the clamps of a tensile testing platform (Model 42, MTS Criterion). Extension at strain rate of 0.5%/s was continuously applied until the dura mater sample failed. The thickness of the dura mater sample was determined from optical micrographs. During the process of mounting and stretching, the dura mater sample was kept hydrated with saline dispensed from a micropipette.

The stress(strain) response plotted FIG. 13B for spinal tissues was adapted from (27).

Animal Groups and Surgical Procedures

All surgical procedures were performed in accordance with Swiss federal legislation and under the guidelines established at EPFL. Local Swiss Veterinary Offices approved all the procedures. Experiments were performed on Lewis rats (LEW/ORlD with initial weight of 180-200 g.

Animal Groups

In the biocompatibility study, rats received either a sham (n=4), stiff (n=4) or soft (n=4) implant. Prior to surgery rats were handled and trained daily in the locomotor tasks for three weeks. These tasks included walking overground along a straight runway, and crossing a horizontal ladder with irregularly spaced rungs. Prior to the training, rats underwent a mild food deprivation and were rewarded with yoghurt at the end of each trial. The body weight was monitored closely; in case of weight loss the food deprivation was adjusted. The animals were terminated 6 weeks post-implantation.

Histology and Morphology of Explanted Spinal Cord
Fixation and Explantation

Figure 20:
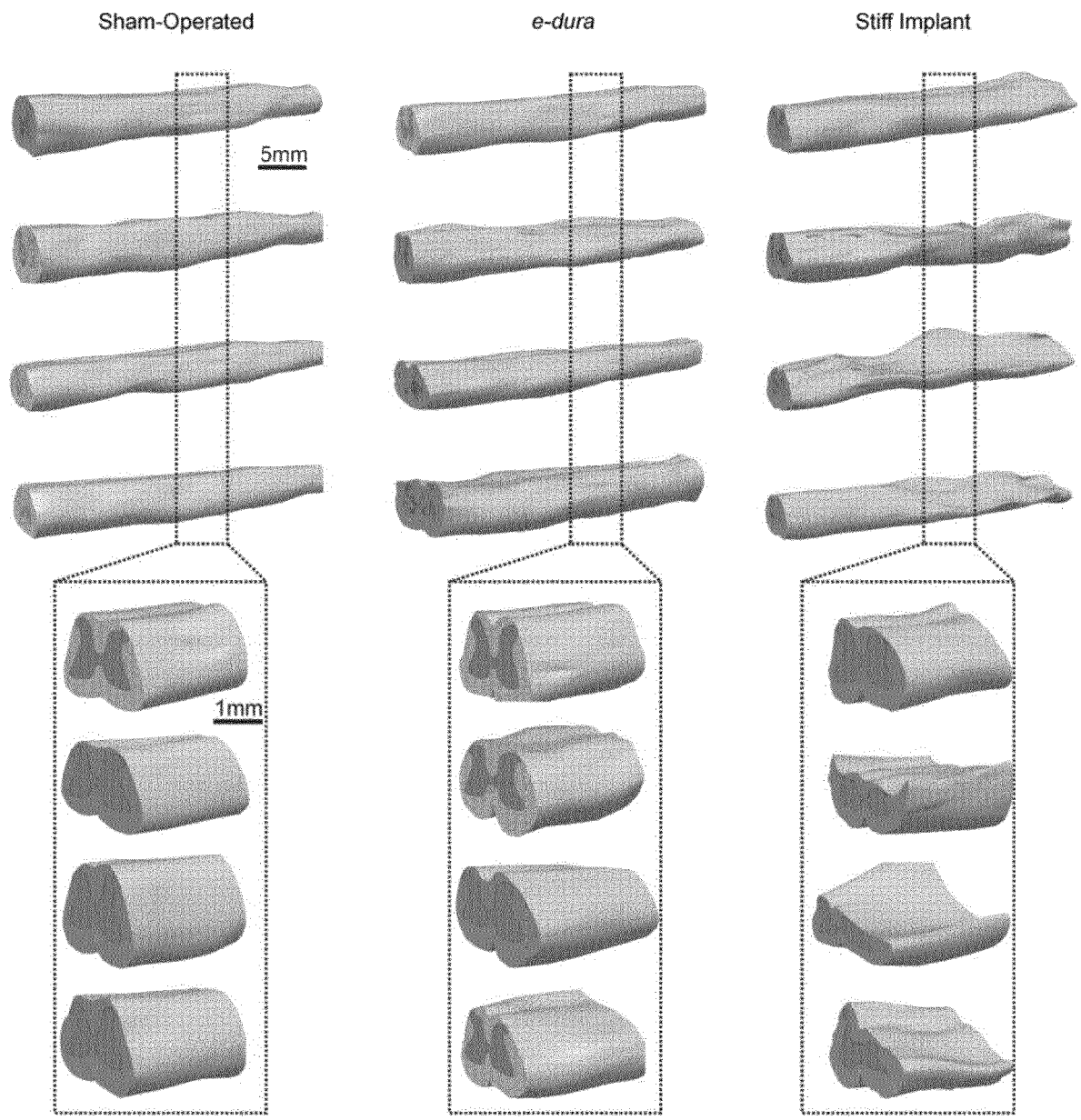

At the end of the experimental procedures, rats were perfused with Ringer's solution containing 100 000 IU/L heparin and 0.25% NaNO2 followed by 4% phosphate buffered paraformaldehyde, pH 7.4 containing 5% sucrose. The spinal cords were dissected, post-fixed overnight, and transferred to 30% phosphate buffered sucrose for cryoprotection. After 4 days, the tissue was embedded and the entire lumbosacral tract sectioned in a cryostat at a 40 µm thickness 3D Reconstruction of the Spinal Cord (FIG. 14B, FIG. 20)

To assess spinal cord morphology, a Nissl staining was performed on 25 evenly spaced lumbosacral cross-sections separated by 0.8 mm, for each rat. The slides were assembled into the Neurolucida image analysis software (MBF Bioscience, USA) to reconstruct lumbosacral segments in 3D. Spinal cord compression was quantified using a circularity index defined as $4\pi$ area/perimeter2. Circularity index was measured for all the slices, and averaged for each rat to obtain a mean value that was compared across groups.

Figure 21:
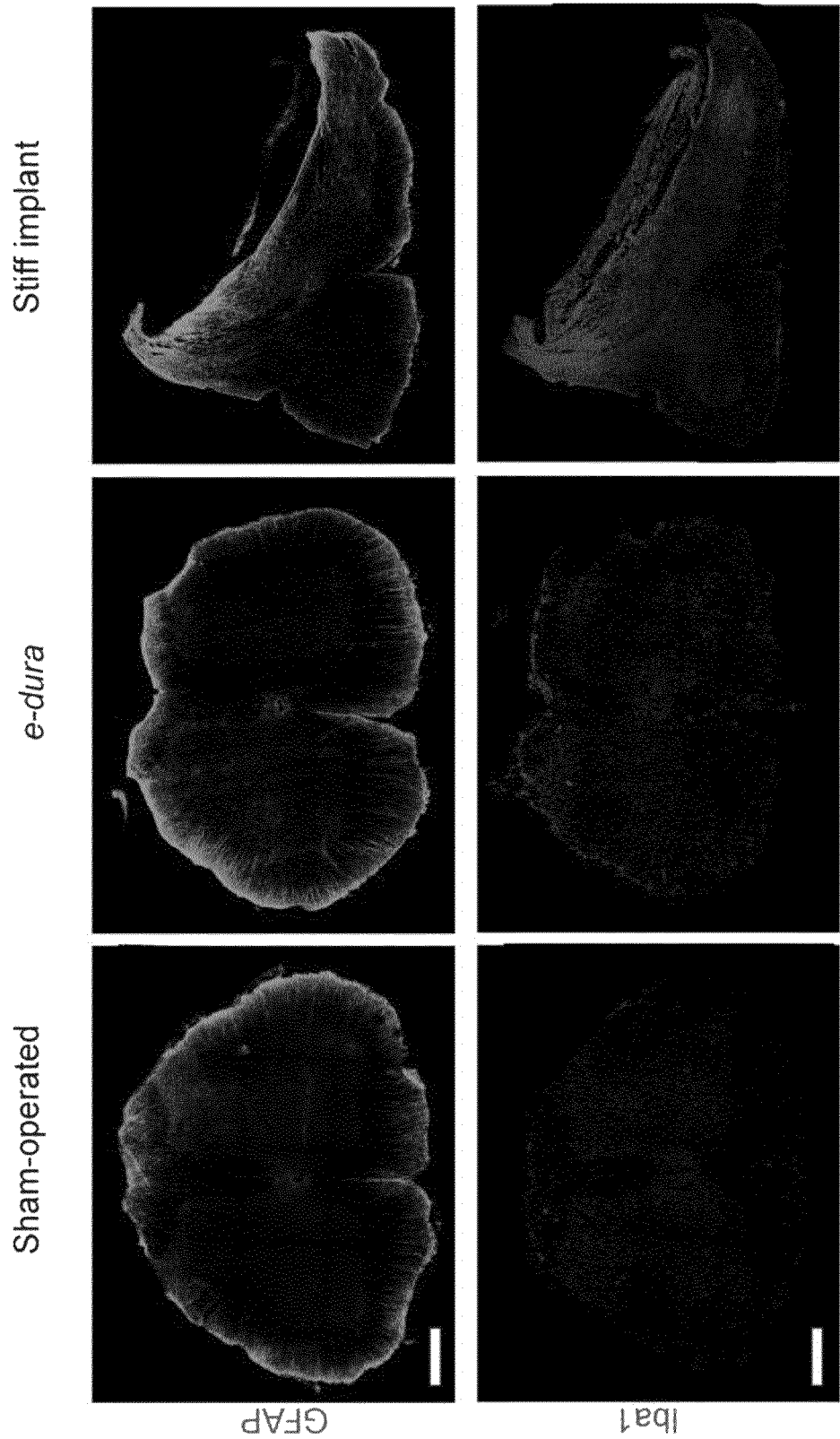

Immunohistochemistry Protocols (FIG. 14C, FIG. 21)

Microglial and astrocytic reactivity was revealed by performing immunohistological staining against glial fibrillary acidic protein (GFAP) and ionized calcium binding adapter molecule 1 (lba1), respectively. Briefly, lumbosacral spinal cord coronal sections were incubated overnight in serum containing anti-lba1 (1:1000, Abcam, USA) or anti-GFAP (1:1000, Dako, USA) antibodies. Immunoreactions were visualized with appropriate secondary antibodies labeled with Alexa fluor® 488 or 555. A fluorescent counterstaining of the Nissl substance was performed with the Neurotrace 640/660 solution (1:50, Invitrogen, USA). Sections were mounted onto microscope slides using anti-fade fluorescent mounting medium and covered with a cover-glass. The tissue sections were observed and photographed with a laser confocal fluorescence microscope (Leica, Germany).

Immunostaining Quantification

Immunostaining density was measured offline using 6 representative confocal images of lumbosacral segments per rat. Images were acquired using standard imaging settings that were kept constant across rats. Images were analyzed using custom-written Matlab scripts according to previously described methods (8). Confocal output images were divided into square regions of interest (ROI), and densities computed within each ROI as the ratio of traced fibers (amount of pixels) per ROI area. Files were color-filtered and binarized by means of an intensity threshold. Threshold values were set empirically and maintained across sections, animals and groups. All the analyses were performed blindly.

In-Vivo Implant Imaging (FIG. 13F)

Imaging of implanted e-dura (5 weeks post implantation) was conducted. Rats were kept under Isoflurane anesthesia during the scan to reduce motion artifacts. Scanner settings were adjusted to avoid artefacts induced by metallic parts of the spinal orthosis (typical settings were: 1 mm aluminum filter, voltage 100 kV, current 100 µA, exposure time 120 ms, rotation step 0.5). Prior to imaging, a contrast agent (Lopamiro 300, Bracco, Switzerland) was injected through the microfluidic channel of the implants to enable visualization of soft tissues and e-dura. Segmentation and 3D model were constructed with Amira® (FEI Vizualisation Sciences Group, Burlington, USA).

Figure 26:
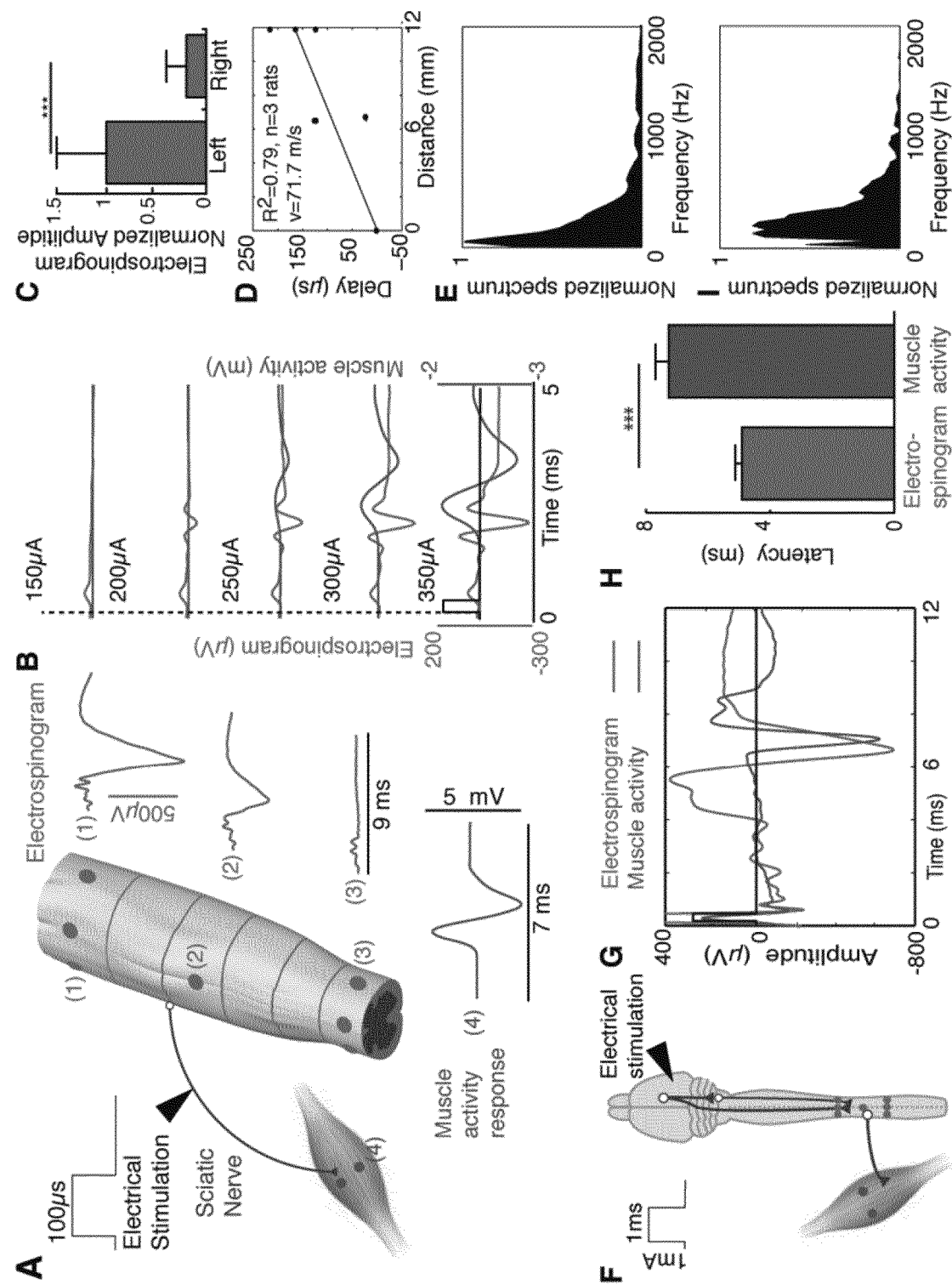

Chronic Recordings of Electrospinograms (FIG. 16C, FIG. 26)

Recordings of electrical potentials from the electrodes integrated in the chronically implanted e-dura, which we called electrospinograms, were performed after 6 weeks of implantation (n=3 rats). Experiments were performed under urethane (1 g/kg, i.p.) anesthesia. Both electrospinograms and muscle activity were recorded in response to stimulation delivered to peripheral nerve or motor cortex. The sciatic nerve was exposed, and insulated from the surrounding tissue using a flexible plastic support. A hook electrode was used to deliver single biphasic pulses of increasing amplitude, ranging from 150 to 350 µA, and 100 µs pulse-width, at 0.5 Hz. Each trial was composed of at least 30 pulses. Responses measured in chronically implanted muscles and from each electrode integrated in the e-dura, were extracted and triggered-averaged. To elicit a descending volley, a custom-made wire electrode was inserted overlying the leg area of the motor cortex, in direct contact with the dura mater. Current controlled bi-phasic pulses were delivered every minute using a 1 mA, 1 ms pulse-width stimulus. Responses were then extracted, and triggered-averaged. Signals were recorded using a TDT RZ2 system (Tucker Davis Technologies), amplified with a PZ2 Pre-amplifier, and sampled at 25 kHz with a digital band-passed filtered (1-5000 Hz). Electrospinograms were recorded differentially from each active site of the implants with respect to a reference fixed to one of the bony vertebrae. The latency, amplitude, and amplitude density spectrum of the recorded signals were analyzed offline.

Electrochemical Stimulation of the Spinal Cord (FIG. 16E, FIG. 27)

Electrochemical stimulation protocols were selected based on an extensive amount of previous studies in rats with spinal cord injury (8, 24, 25). The chemical stimulation used during training was administered through the microfluidic channel integrated in the chronically implanted e-dura. After 1-2 minutes, subdural electrical stimulation currents were delivered between active electrodes located on the lateral aspect or midline of sacral (S1) and lumbar (L2) segments, and an indifferent ground located subcutaneously. The intensity of electrical spinal cord stimulation was tuned (40 Hz, 20-150 µA, biphasic rectangular pulses, 0.2 ms duration) to obtain optimal stepping visually. To demonstrate the synergy between chemical and electrical stimulation, we tested rats without any stimulation, with chemical or electrical stimulation alone, and with concurrent electrochemical stimulation. To demonstrate the previously inaccessible capacity to facilitate specific aspects of locomotion with subdural electrical stimulation, we delivered electrical stimulation using electrodes located on the lateral aspects of lumbar and sacral segments, and compared locomotor movements with stimulation delivered bilaterally.

e-dura bio-integration. We tested the biocompatibility of the soft e-dura implant compared to a stiff implant under chronic conditions (6 weeks). We fabricated a stiff implant using a 25 µm thick polyimide film, which corresponds to standard practices for flexible neural implants (19) and is robust enough to withstand the surgical procedure. We inserted both types of implant into the subdural space of lumbosacral segments in healthy rats, and prepared sham-operated animals that received the headstage, connector, and vertebral orthosis but without spinal implant.

Figure 19:
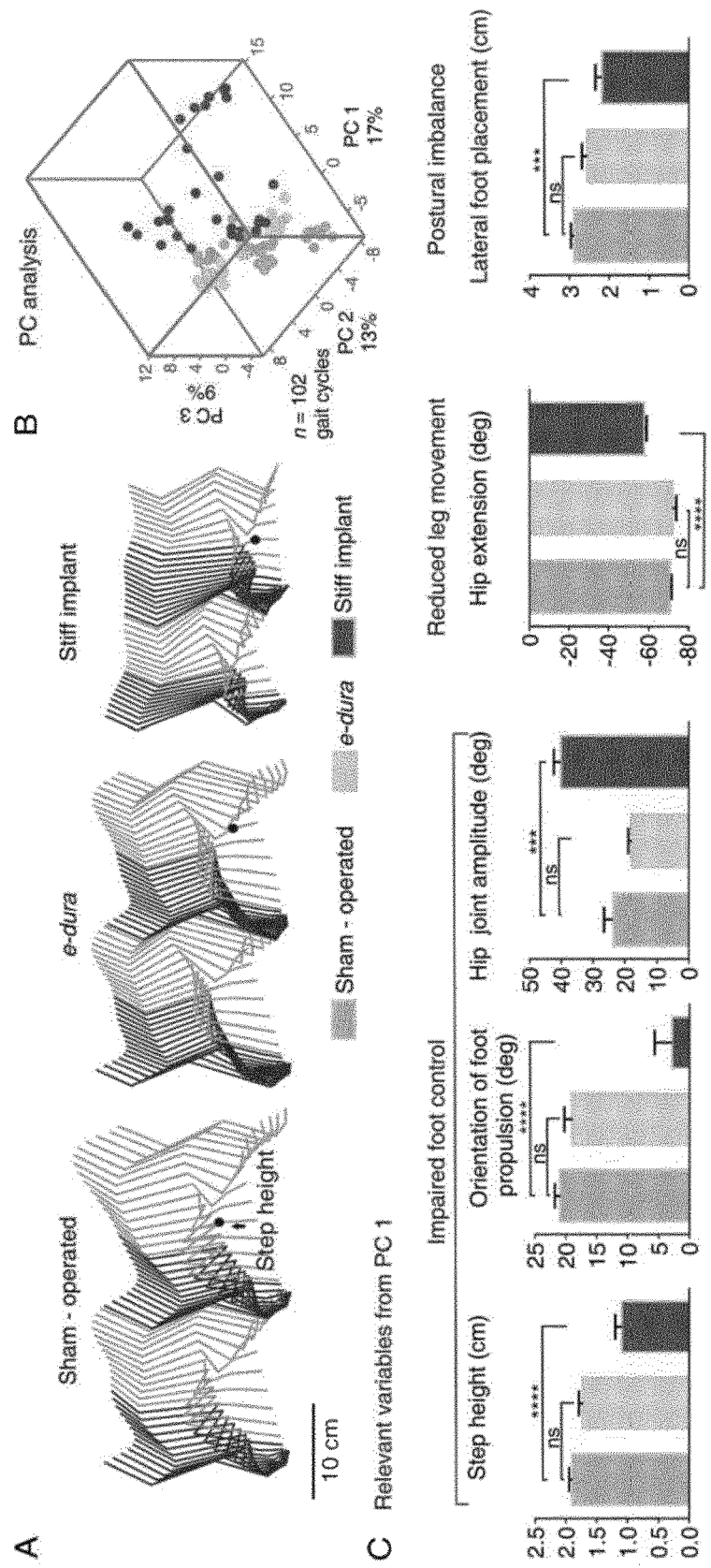

To assess motor performance, we conducted high-resolution kinematic recordings of whole-body movement during basic walking and skilled locomotion across a horizontal ladder. In the chronic stages, the behavior of rats with soft implants was indistinguishable from that of sham-operated animals (FIG. 14A, FIG. 19). By contrast, rats with stiff implants displayed significant motor deficits that deteriorated over time. They failed to accurately position their paws onto the rungs of the ladder (FIG. 14A). Even during basic walking, rats with stiff implants showed pronounced gait impairments including altered foot control, reduced leg movement, and postural imbalance (FIG. 19).

The spinal cords were explanted after 6 weeks of implantation. Both soft and stiff implants occupied the targeted location within the subdural space. We observed minimal connective tissue around the implants. To evaluate potential macroscopic damage to spinal cord that may explain motor deficits, we reconstructed the explanted lumbosacral segments in 3D, and calculated a cross-sectional circularity index to quantify changes in shape. All the rats with stiff implants displayed significant deformation of spinal segments under the implant (p<0.001, FIG. 14B), ranging from moderate to extreme compression (FIG. 20).

Neuro-inflammatory responses at chronic stages were then visualized using antibodies against activated astrocytes and microglia (FIG. 14C), two standard cellular markers for foreign body reaction (12). As anticipated from macroscopic damage, both cell types massively accumulated in the vicinity of stiff implants (p<0.05, FIG. 14C, FIG. 21). In striking contrast, no significant difference was found between rats with soft implants and sham-operated animals (FIG. 14C, FIG. 21). These results demonstrate the chronic biocompatibility of the soft implants according to the present invention.

Patterning extremely thin plastic films in web-like systems offers alternative mechanical designs for implants conforming to dynamically deforming tissue (20). However, this type of interfaces requires complex, multi-step processing and transient packaging. In comparison, fabrication steps of e-dura according to the present invention are remarkably simple. Moreover, the e-dura topology and unusual resilience greatly facilitates surgical procedures.

e-dura properties. The electrochemical and electromechanical behavior of the platinum-silicone composite electrodes and of the chemotrodes according to the present invention was next characterized, both in vitro and in vivo. The composite electrodes displayed low impedance (Z=5.2±0.8 kΩ at 1 kHz, n=28 electrodes), and maintained the electrochemical characteristics of platinum (FIG. 15A-B). Cyclic voltammograms of the composite electrodes remained unchanged when the implant was stretched up to a strain of 45%. The high effective surface area of the platinum-silicone composite produced a large cathodal charge storage capacity of 46.9±3.3 mC/cm2. This value is two orders of magnitude higher than that of smooth platinum (21), and is smaller but comparable to that of highly doped organic electrode coatings (22).

The efficacy of charge injection was tested as well. The composite electrode supported charge injection limit of 57±9 µC/cm2, which is comparable to the injection limit of platinum (21) (FIG. 15C, FIG. 22). These characteristics remained stable even after five million electrical pulses, which corresponds to more than 30 hours of continuous stimulation with clinically relevant parameters (40 Hz, charge-balanced, biphasic, 100 µA current pulse, 0.2 ms pulse width).

Figure 24:
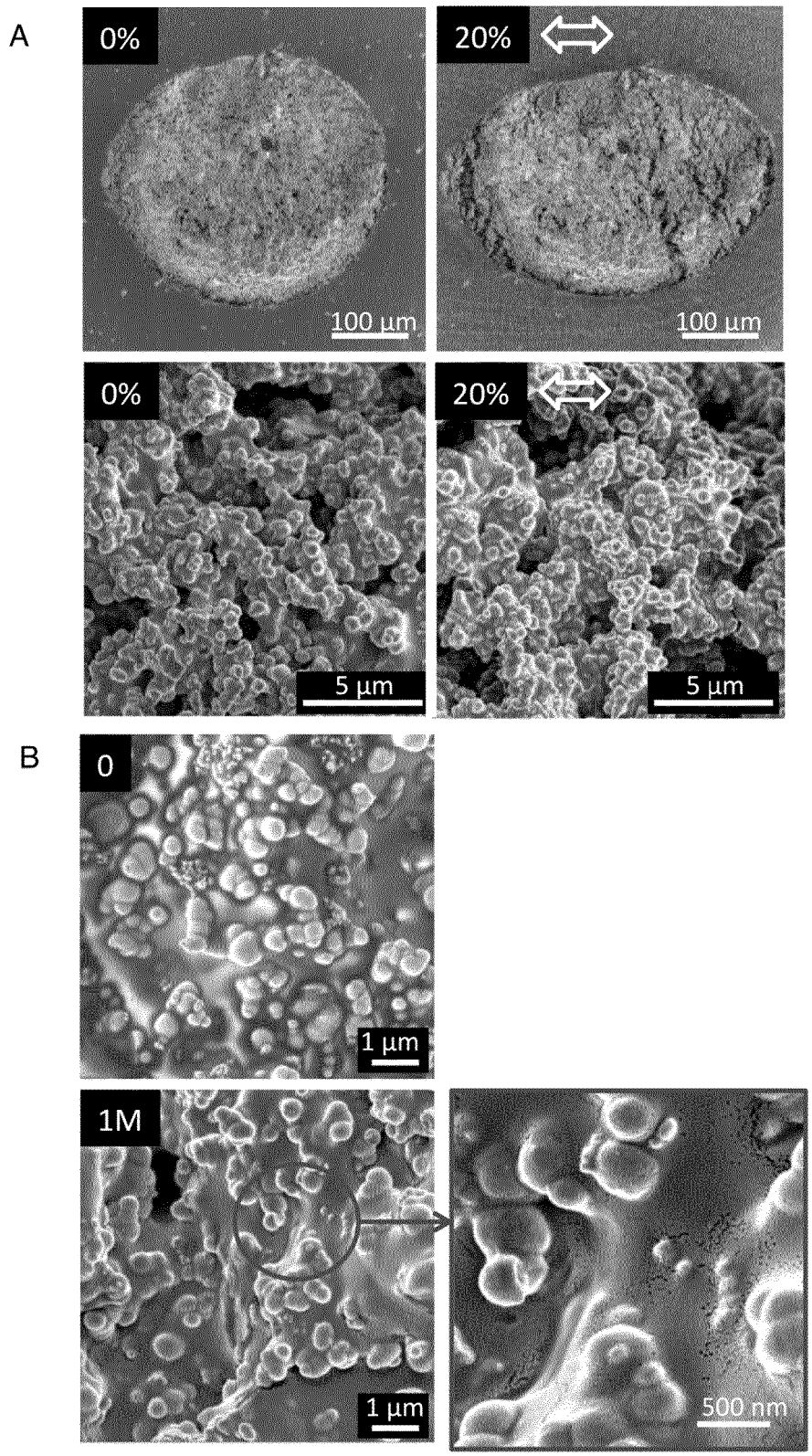

To demonstrate the robustness of e-dura against deformation experienced by natural dura mater during daily living activities, the device was stretched to 20% strain over one million cycles. The implant, the chemotrode, and the seven embedded electrodes withstood the cyclic deformation, displaying minimal variation in impedance over time (FIG. 15D, FIG. 23-24). Assuming radical postural changes approximately every 5 minutes, these results indicate that the e-dura would survive mechanically for nearly a decade in a patient.

Finally, electrode impedance and chemotrode functionality was monitored over time in 4 chronically implanted rats (n=28 electrodes and 4 chemotrodes in total). Impedance at 1 kHz remained constant throughout the 5 weeks of evaluation (FIG. 15E), demonstrating stability of stretchable electrodes in vivo. Daily injections of drugs and hydrodynamic evaluations of microfluidic channels after explantation (FIG. 17) confirmed that the chemotrodes remain operational for extended durations in vivo.

These combined results demonstrate electrochemical stability, mechanical robustness, and long-term functionality of the e-dura electrodes and chemotrodes according to the present invention, abiding the challenging requirements for chronic implantation.

e-dura applications. The advanced capabilities of e-dura according to the present invention was demonstrated for basic neuroscience and neuroprosthetics. An e-dura implant according to the present invention was fabricated, consisting of a 3×3 electrode array, which was placed over the motor cortex of mice expressing channelrhodopsin ubiquitously (FIG. 16A). The silicone substrate is optically transparent, enabling concurrent optical stimulation and neural recording. To activate neurons, the cortical surface was illuminated with a laser focused on distinct locations. The spatial resolution of electrocorticograms recorded from the e-dura allowed extraction of neuronal activation maps that were specific for each site of stimulation (FIG. 16A).

Figure 18:
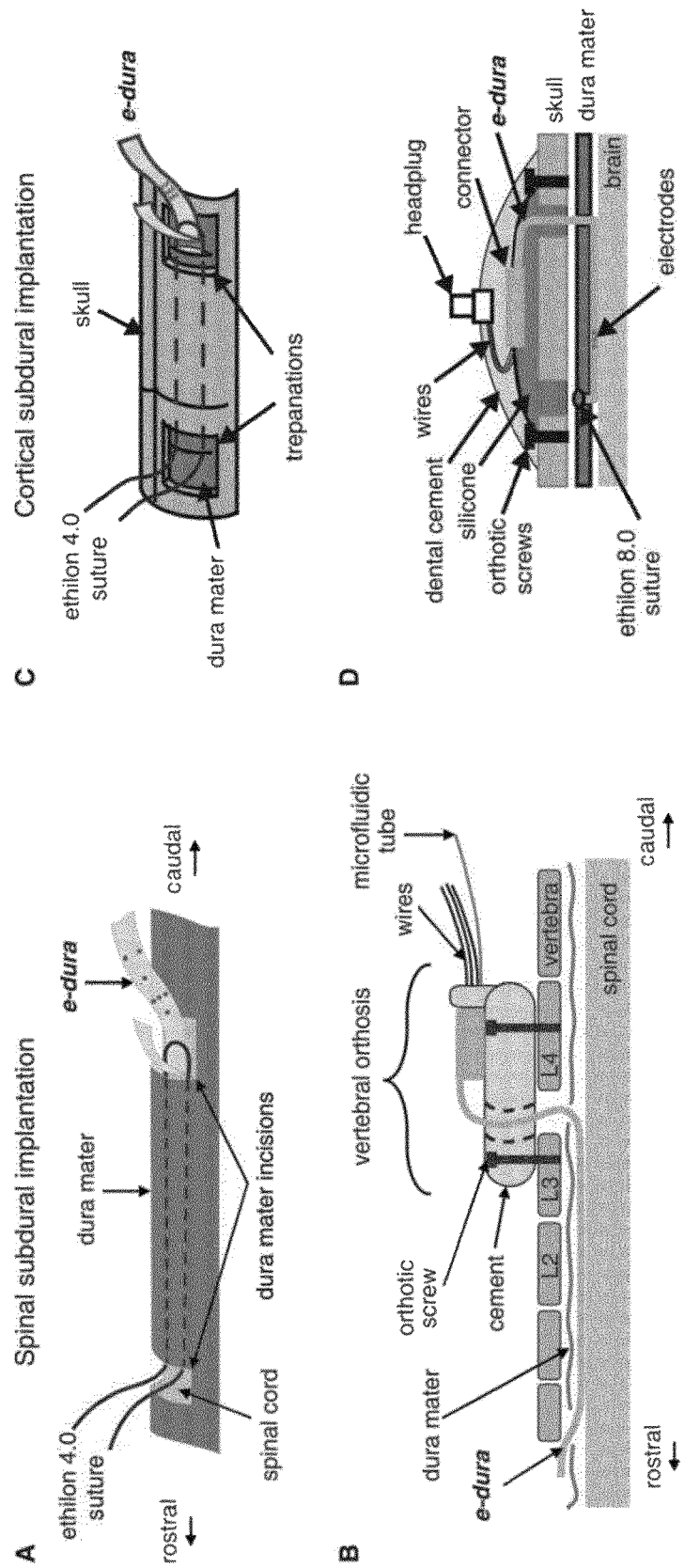
Figure 25:
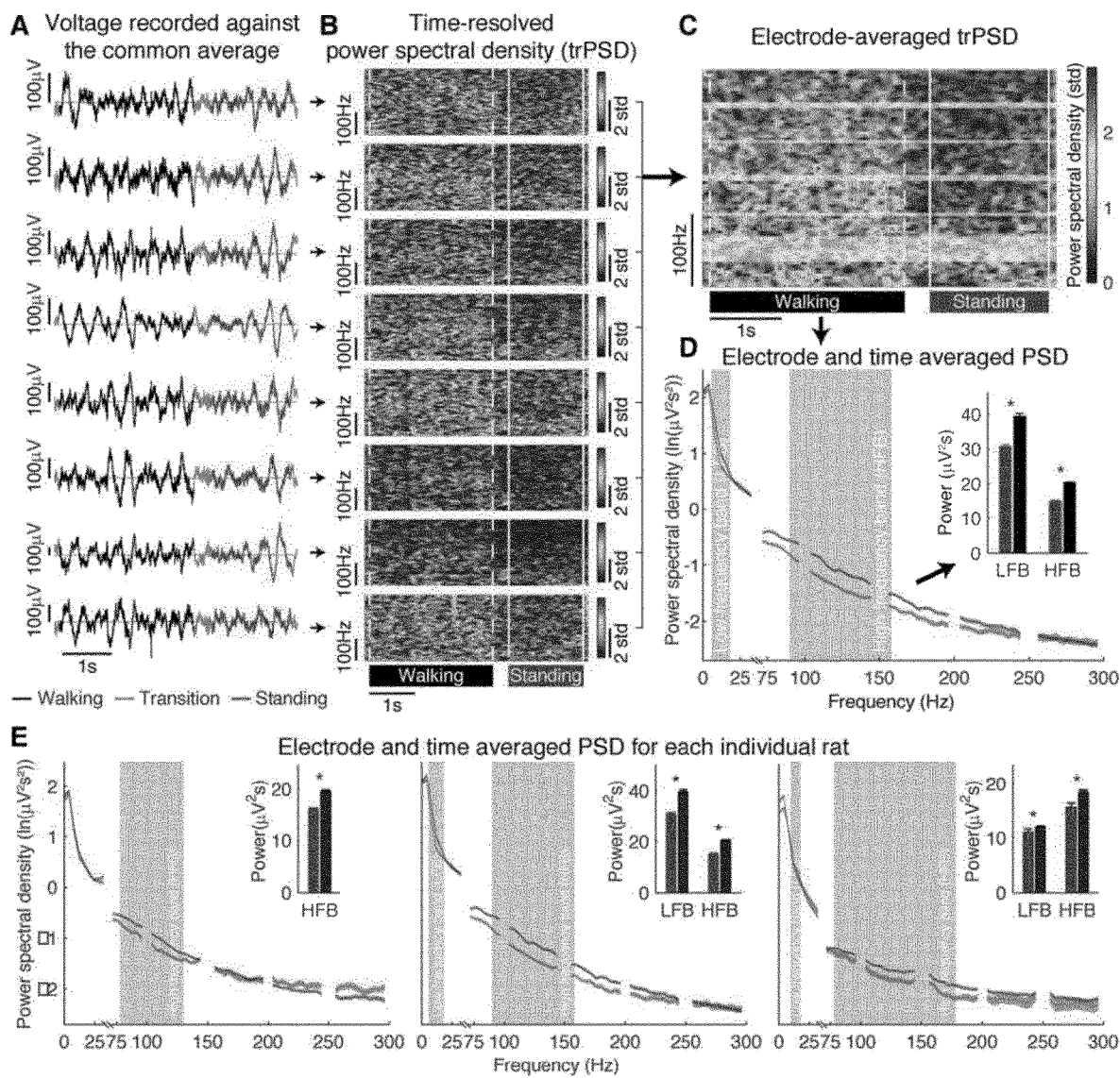

An e-dura implant according to the invention was chronically implanted between the dura mater and motor cortex tissues (FIG. 18), and electrocorticograms were recorded in conjunction with whole-body kinematic and leg muscle activity in freely moving rats (FIG. 16B). Power spectral density analysis applied on electrocorticograms (23) clearly identified standing and locomotor states over several weeks of recordings (FIG. 16B, FIG. 25). To verify whether neural recordings could also be obtained from an e-dura chronically implanted over spinal tissues, electrospinograms elicited from electrical stimulation of the motor cortex or the sciatic nerve were measured. Descending motor command was reliably recorded (FIG. 26), and peripheral sensory feedback was detected with remarkable spatial and temporal selectivity after 6 weeks of implantation (FIG. 16C, FIG. 26).

Figure 28:
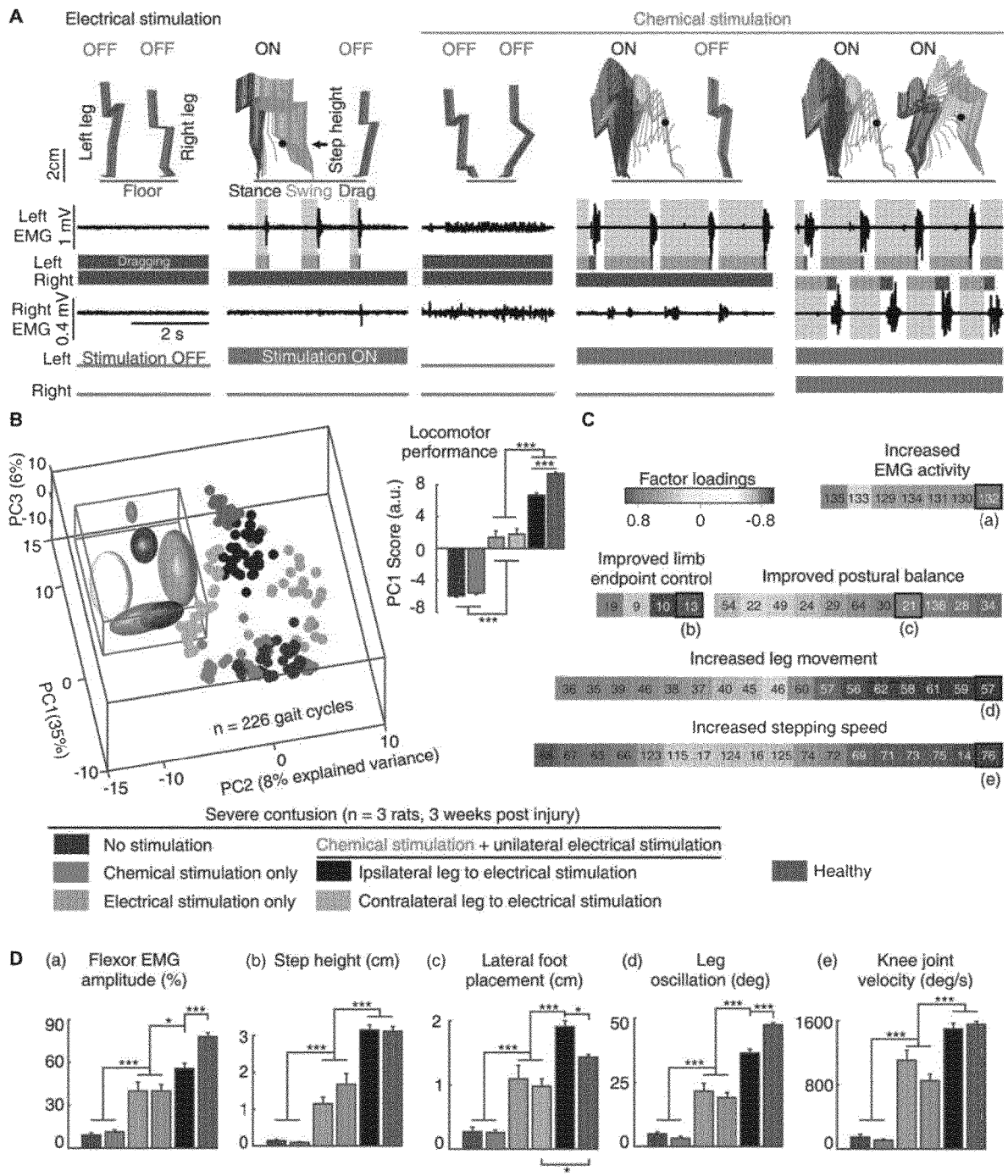

The e-dura was exploited to restore motor control after spinal cord injury (8, 17). Adult rats received a clinically relevant contusion at the thoracic level, which spared less than 10% of spinal tissues at the lesion epicenter, and led to permanent paralysis of both legs (FIG. 16D). Use was made of the chronic spinal e-dura (FIG. 13) to engage spinal locomotor circuits located below injury. A serotonergic replacement therapy (5HT1A/7 and 5HT2 agonists) (24) was injected through the chemotrode, and delivered continuous electrical stimulation using the soft electrodes located on the lateral aspect of L2 and S1 segments (40 Hz, 0.2 ms, 50-150 µA) (25). The concurrent electrical and chemical stimulations instantly enabled the paralyzed rats to walk (FIG. 16E). Intrathecal delivery allowed a 5-fold reduction of injected drug volume compared to intraperitoneal injection required to obtain the same facilitation of stepping (FIG. 27). Subdural drug delivery through the chemotrode annihilated side effects of serotonergic agents on autonomic systems (FIG. 27). The distributed electrodes of the e-dura delivered stimulation restricted to specific segments, which allowed facilitation of left versus right leg movements (FIG. 28). The soft electrochemical neuroprosthesis mediated reliable therapeutic effects during the 6-week rehabilitation period.

Soft neural implants have been introduced that are chronically bio-integrated within the central nervous system. It was demonstrated that biomechanical coupling between implants and neural tissues is critical to obtain this symbiosis. The subdural implantation of e-dura limits foreign body reaction and reduces drug side effects. This location enables high-resolution neuronal recordings, and concurrent delivery of electrical and chemical neuromodulation alleviating neurological deficits for extended periods of time. Future neuroprosthetic medicine will require chronic, multimodal, and bidirectional communication between implants and neural tissues (1). e-dura provides a novel platform to design these types of neural interfaces integrating electrodes, chemotrodes, and potentially optrodes for basic research and neuroprosthetics. While challenges lie ahead, e-dura according to the present invention holds promises for a new generation of diagnostic and clinical interfaces.

Figure 13:
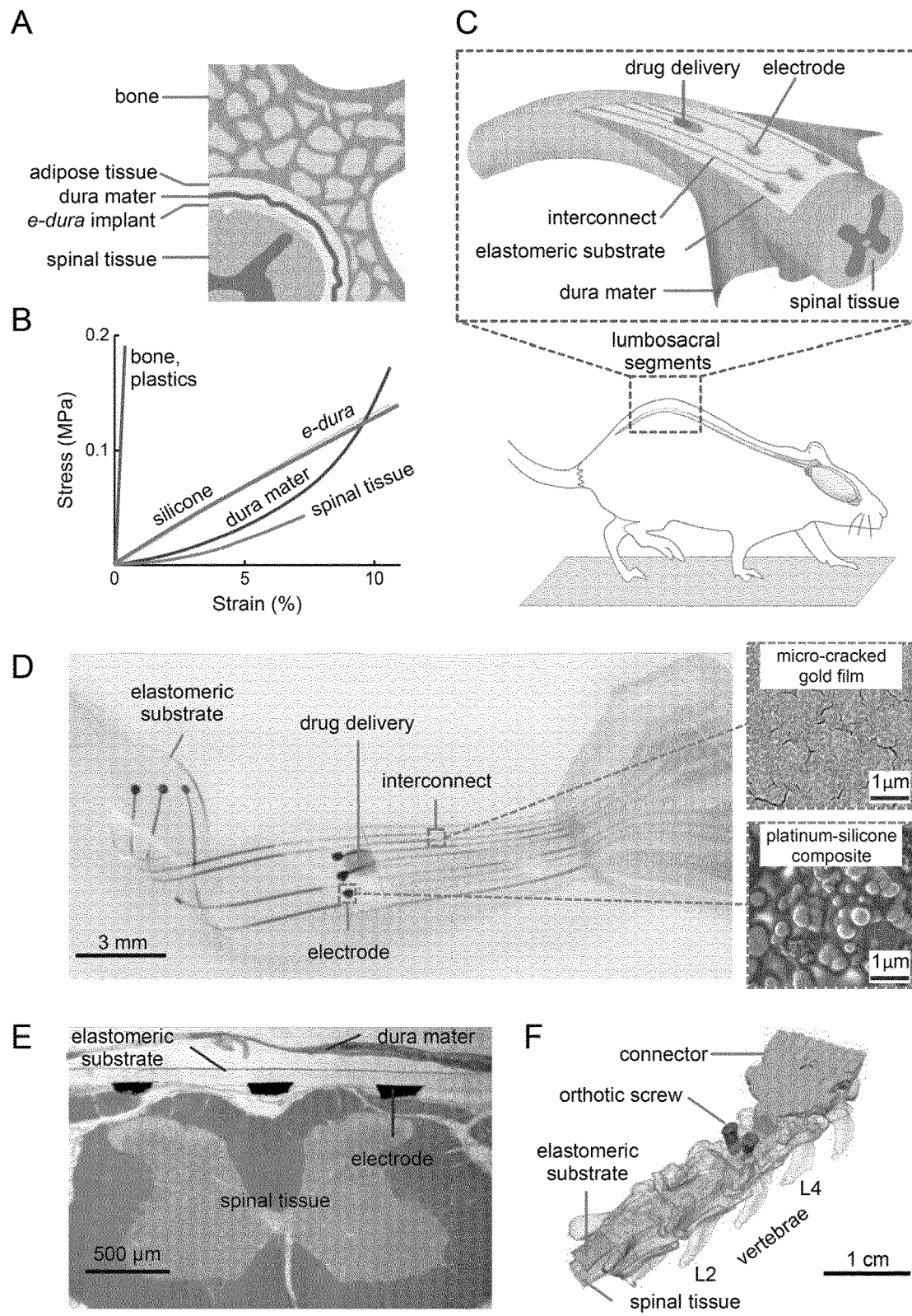

FIG. 13. Electronic dura mater, "e-dura", tailored for the spinal cord. (A) Schematic cross-section of the vertebral column with the soft implant inserted in the spinal subdural space. (B) Strain-stress curves of spinal tissues, dura mater, implant materials, and complete e-dura. Plastics (polyimide), silicone, e-dura and dura mater responses are experimental data. Spinal tissue response is adapted from the literature (see Suppl. data). (C) Illustration of the e-dura implant inserted in the spinal subdural space of rats. (D) Optical image of an implant, and micrographs of the gold film and the platinum-silicone composite. (E) Cross-section of an e-dura inserted in the spinal subdural space during 6 weeks. (F) Reconstructed 3D Micro-Computed Tomography scans of the e-dura inserted in the spinal subdural space covering L2 to S1 spinal segments in rats. The scan was obtained in vivo at week 5 after implantation.

Figure 14:
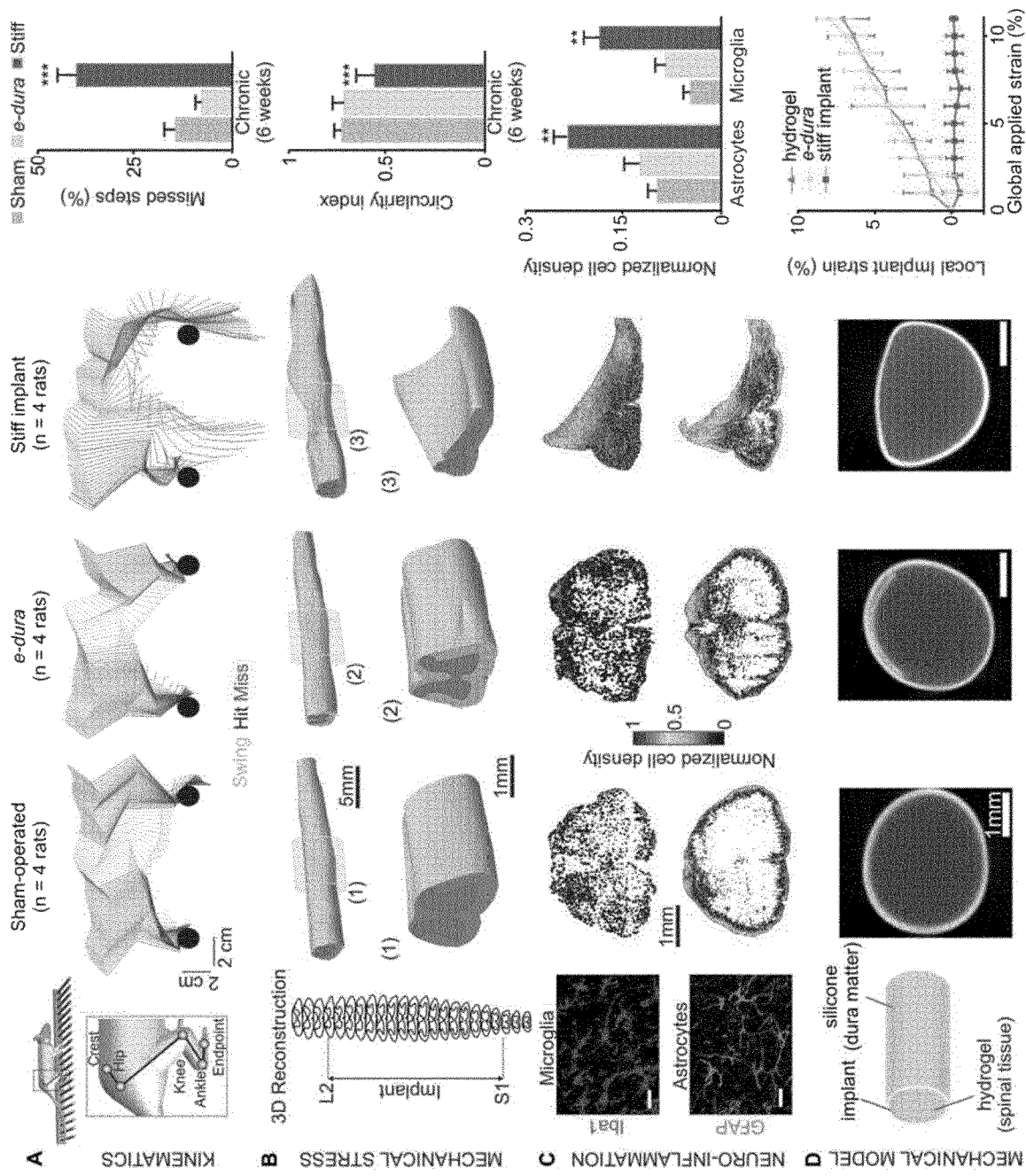

FIG. 14. e-dura biointegration. (A) Hindlimb kinematics during ladder walking 6 weeks post-implantation. Histogram plots reporting mean percentage of missed steps onto the rungs of the ladder (n=8 trials per rat, n=4 rats per group). (B) 3D spinal cord reconstructions, including enhanced views, 6 weeks post-implantation. Bar plots reporting mean values of spinal cord circularity index ($4\pi \times$ area/perimeter2). (C) Photographs showing microglia (Iba1) and astrocytes (GFAP) staining reflecting neuro-inflammation. Scale bars: 30 µm. Heat maps and bar plots showing normalized astrocyte and microglia density. (D) Spinal cord model scanned using Micro-Computed Tomography without and with a soft or stiff implant. e-dura implant is 120 µm thick. The red line materialized the stiff implant (25 µm thick), not visualized due to scanner resolution. Plot reporting local longitudinal strain as a function of global strain. $P<0.01$; *$P<0.001$. Error bars: SEM.

FIG. 15. Properties of e-dura electrodes. (A) Magnitude and phase of electrode impedance recorded in phosphate buffer saline solution (pH 7.4). Spectra were collected before (■), at maximum elongation (▼), and after (○) a uniaxial stretch cycle to 45% strain. Stretch is observed to reversibly affect the resistance of the stretchable interconnect. (B) Cyclic voltammograms recorded in N2 purged, diluted sulfuric acid (pH 0.9) and during a uniaxial stretch cycle to 45% strain. Slow sweep cyclic voltammetry (50 mV/s) reveals high current densities through the electrode even at large tensile strain. The peaks correspond to oxide formation (*), oxide reduction (**), H+ adsorption (◇◇), and H+ desorption (◇) on Pt metal surfaces. (C) Charge injection limit of electrodes (n=4, ±S.D.) and evolution following repeated pulse delivery. (D) Relative impedance modulus of electrodes (n=7, ±S.D.) recorded at 1 kHz and at rest and following uni-axial fatigue cycling to 20% strain. Inset: Scanning electron micrographs of an electrode after the first and one millionth stretch cycles. (E) Modulus and phase angle of the impedance vector at 1 kHz (n=28 total electrodes, ±S.D, across 4 rats) recorded in vitro, then in vivo immediately after implantation and weekly until terminal procedure.

Figure 16:
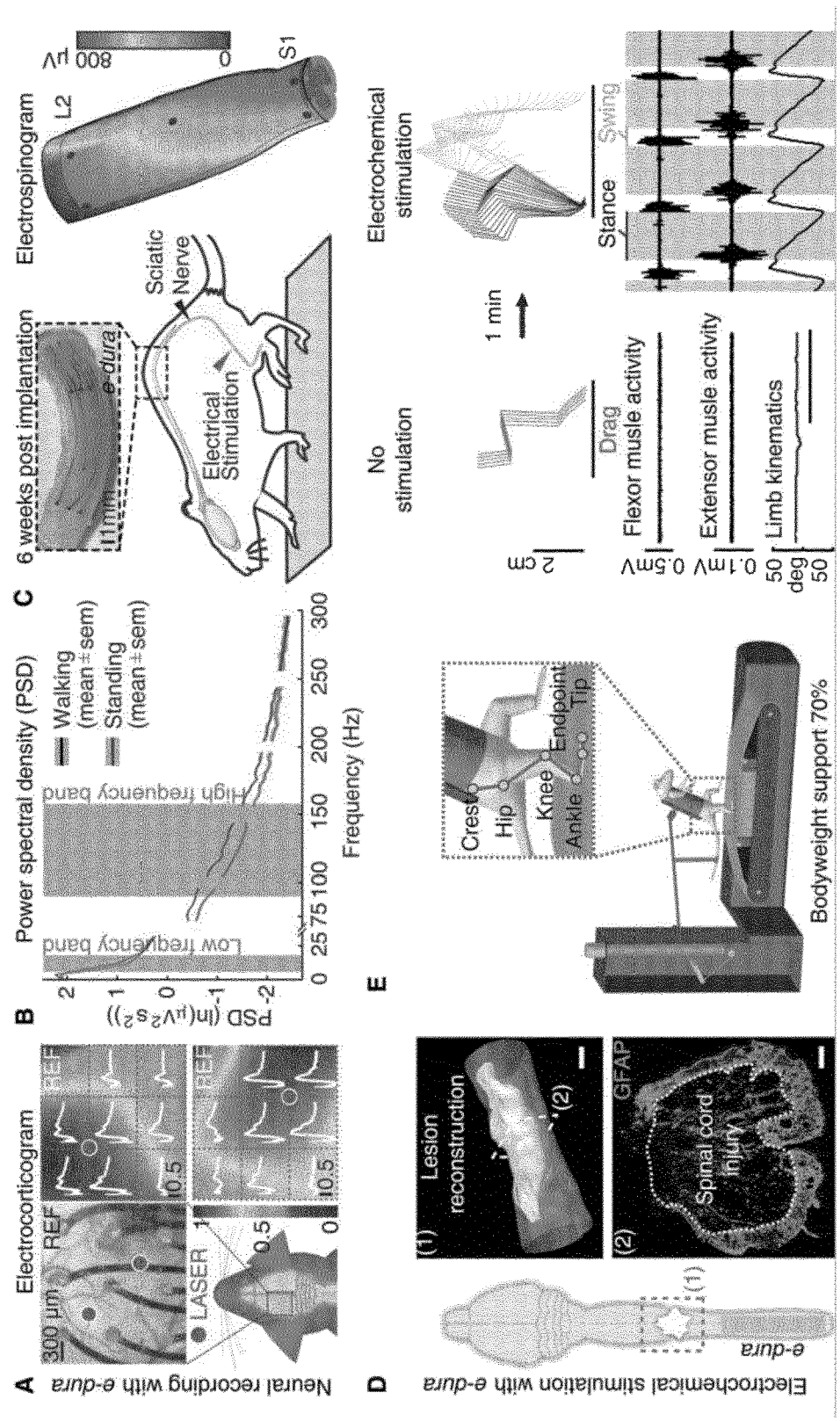

FIG. 16. Recordings and stimulation with e-dura. (A) e-dura implant positioned over the cortical surface of a Thy1-ChR2-YFP mouse. Blue spot indicates laser location. Cortical activation maps were reconstructed from normalized electrocorticograms, shown in white (150 µs duration). (B) Power spectral density computed from motor cortex electrocorticograms recorded 3 weeks after e-dura implantation in rats. Increased neural activity in low and high frequency bands differentiate cortical states during walking from standing. (C) Spinal cord activation map was reconstructed from electrospinograms recorded 6 weeks after e-dura implantation in response to left sciatic nerve stimulation. (D) Rats were chronically implanted with a spinal e-dura covering lumbosacral segments, and received a severe spinal cord injury. (E) Recording without and with electrochemical stimulation during bipedal locomotion under robotic support after 3 weeks of rehabilitation. Stick diagram decompositions of hindlimb movements are shown together with leg muscle activity and hindlimb oscillations.

Figure 17:
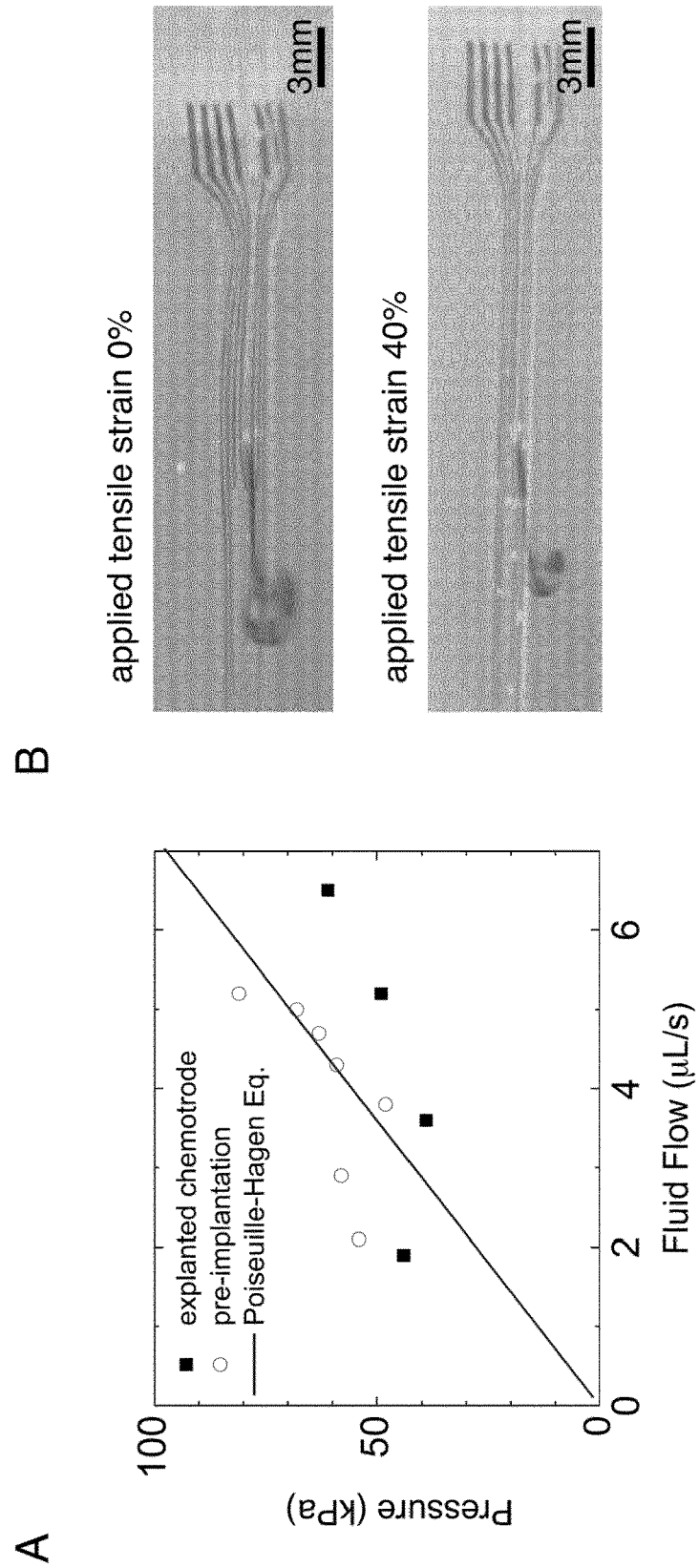

FIG. 17. e-dura chemotrode: compliant fluidic microchannel. (A) Determination of the hydrodynamic resistance of the microfluidic system. The continuous line displays the fluid flow predicted by the Poiseuille-Hagen equation. Monitoring the hydrodynamic response of the chemotrode before surgery and after explantation following 6 weeks of chronic implantation demonstrated that the microfluidic channels do not become occluded with tissue or debris, and maintain functionality during prolonged subdural implantation. (B) Blue-colored water was injected through the chemotrode under different tensile conditions. The integrity and functionality of the microfluidic channel was maintained when the implants was stretched up to a strain of 40%.

FIG. 20. Damage of spinal tissues after chronic implantation of stiff, but not soft, implants. 3D reconstructions of lumbosacral segments for all 16 tested rats (3 groups of 4 animals), including enhanced views. The spinal cords were explanted and reconstructed through serial Nissl-stained cross-sections after 6-week implantation. Stiff implants induced dramatic damage of neural tissues, whereas the e-dura had a negligible impact on the macroscopic shape of the spinal cord.

FIG. 21. Significant neuro-inflammatory responses after chronic implantation of stiff, but not soft, implants. Cross-section of the L5 lumbar segment stained for the neuro-inflammatory markers GFAP (astrocytes) and Iba1 (microglia) after 6-week implantation. A representative photograph is shown for each group of rats. The stiff implant leads to a dramatic increase in the density of neuro-inflammatory cells, whereas the e-dura had a negligible impact on these responses. Scale bars: 500 µm.

FIG. 22. Determination of charge injection capacity of electrodes with platinum-silicone coating. (A) Charge-balanced, biphasic current pulses were injected through electrodes immersed in saline electrolyte (PBS). The duration of each pulse phase was fixed at 200 µs per phase, which corresponds to the typical pulse duration used during therapeutic applications. (B) The amplitude of the current pulses was gradually increased. As the current density flowing through the coating and its polarization increased, a significant portion of the recorded voltage drop occurred in the electrode interconnects and the electrolyte above the coating. (C) To obtain the true voltage transients at the coating surface with respect to the reference electrode, the instantaneous polarization of the cell was subtracted. The maximum safe current density was reached when the coating polarization exited the water window.

FIG. 23. Impedance spectroscopy of the soft electrodes under cyclic stretching to 20% strain. (A) Apparatus for conducting electrochemical characterization of soft implants under tensile strain. The ends of the implant were glued to two probes that are clamped to the jaws of a custom built extensimeter. The implant and (partially) the probes were then submerged in Phosphate Buffered Saline (PBS). The extensimeter applied pre-defined static strain to the implant, or performed a cyclic stretch-relax program. A counter and a reference electrode were submerged in the electrolyte to complete the circuit (not shown). (B) Representative impedance plots recorded from one electrode. The spectra were recorded at 0% applied strain after 10, 1,000, 10,000, 100,000 and 1 million stretch cycles. Each stretch cycle lasted 1 s. The implants remained immersed in PBS throughout the evaluations. The remaining 6 electrodes in the tested implants exhibited a similar behavior.

FIG. 24. In-situ scanning electron micrographs of platinum-silicone coatings. (A) Images collected during the first stretch cycle to 20% applied strain (from pristine electrode). Low magnification scanning electron micrographs taken at 20% strain revealed the appearance of cracks, but the absence of delamination. The high effective surface area of the composite coating is clearly visible in medium magnification scanning electron micrographs (lower panels). (B) Images collected before (cycle 0) and after one million stretch cycles to 20% strain. All the images were taken at 0% strain. High-magnification scanning electron micrographs revealed the effects of fatigue cycling on the nano-scale morphology of the composite coating.

It has therefore been demonstrated with the above description that methods according to the present invention allow to obtain the wished results, thus overcoming the drawbacks affecting the prior art methods.

Whilst the present invention has been clarified by means of the above description of its embodiments depicted in the drawings, the present invention is not limited to the embodiments depicted in the drawings and/or described above.

The scope of the present invention is rather defined by the appended claims.

The invention claimed is:

1. A method for producing a device adapted to be implanted into the human body, said method comprising:
   providing a stretchable layer or membrane of an insulating material;
   forming on said layer or membrane at least one stretchable conductive path;
   depositing at least one small bolus of a soft and conductive paste or material onto pre-defined areas or portions of said at least one conductive path;
   inserting a first end portion of a conductive element into said at least one small bolus of soft conductive paste or material, wherein:
   a second end portion of said conductive element opposite to said first end portion is not inserted into said at least one bolus;
   said at least one small bolus of soft and conductive paste or material is composed of a blend of electrically conductive nano-micro particles, an elastomer pre-polymer and a crosslinker; and
   crosslinking said elastomer pre-polymer, thereby obtaining a blend of the electrically conductive nano-micro particles and a crosslinked elastomer.

2. The method according to claim 1, wherein said method further comprises providing at least one further electrical device in electrical contact with said second end portion of said at least one conductive element.

3. The method according to claim 2, wherein said at least one further electrical device comprises one of an electrical wire, a PCB, or a chip.

4. The method according to claim 3, said method comprising stripping off insulation of a conductive wire and inserting a resulting exposed end portion of said conductive wire into said at least one bolus of soft conductive paste.

5. The method according to claim 2, said method further comprising flooding said at least one further electrical device with a viscous elastomer.

6. The method according to claim 5, wherein said viscous elastomer comprises one of a silicone elastomer or a similar insulating polymer.

7. The method according to claim 5, said method further comprising curing said elastomer so as to polymerise said elastomer, thus forming an electrically insulating package that mechanically stabilises said at least one electrical device and immobilises both said at least one electrical device and said conductive element and prevents the conductive paste or material from flowing out of said package or shorting said conductive element.

8. The method according to claim 6, said method further comprising exposing at least one portion of said at least one electrical device comprising contact pads or electrodes.

9. The method according to claim 1, said method further comprising forming in said layer or membrane at least one microfluidic channel adapted to deliver and/or collect fluids.

10. The method according to claim 1, said method further comprising embedding in said layer or membrane at least one waveguide.

11. The method according to claim 1, said method comprising forming at least one passivation layer on said at least one conductive path and forming at least one through via in said at least one passivation layer so as to expose at least one of said predefined areas or portions of said at least one conductive paths.

12. A device adapted to be implanted into the human body, said device comprising:
   a stretchable layer or membrane of an insulating material;
   at least one stretchable conductive path on said layer or membrane;
   at least one small bolus of a soft and conductive paste or material onto pre-defined areas or portions of said at least one conductive path, wherein said small bolus of soft conductive paste or material is composed of a blend of electrically conductive nano-micro particles and a crosslinked elastomer; and
   a conductive element, a first end portion of said conductive element being inserted into said at least one bolus of soft conductive paste or material, wherein a second end portion of said conductive element opposite to said first end portion is not inserted into said at least one bolus.

13. The device according to claim 12, wherein said device further comprises at least one further electrical element in electrical contact with soft conductive paste or material with a portion of said at least one further electrical element inserted into an external electrical device.

14. The device according to claim 13, wherein said at least one further electrical device comprises one of an electrical wire, a PCB, and a chip.

15. The device according to claim 13, wherein said at least one further electrical device is embedded in a viscous elastomer.

16. The device according to claim 15, wherein said viscous elastomer comprises one of a silicone elastomer or a similar insulating polymer.

17. The device according to claim 16, wherein said further electrical device comprises at least one exposed portion comprising contact pads, electrodes or the like.

18. The device according to claim 15, said device further comprises a package formed by curing and polymerizing said elastomer, said package thus electrically insulating and mechanically stabilising said at least one further electrical device.

19. The device according to claim 12, said device further comprising at least one microfluidic channel adapted to deliver and/or collect fluids and formed in said layer or membrane.

20. The device according to claim 12, said device further comprising at least one waveguide embedded in said layer or membrane.

21. The device according to claim 12, said device comprising at least one passivation layer on said at least one conductive path and at least one through via in said at least one passivation layer so as to expose at least one of said predefined areas or portions of said at least one conductive path.

22. A method for producing a device adapted to be implanted into the human body, said method comprising:
   providing a stretchable layer or membrane of an insulating material;
   forming on said layer or membrane a stretchable conductive path;
   forming a passivation layer on said conductive path;
   forming a through via in said passivation layer, the through via exposing a portion of said conductive path;
   depositing a bolus of a soft and conductive material into the through via and onto the exposed portion of said conductive path;
   inserting a first end portion of a conductive element into said at least one small bolus of soft conductive paste or material, wherein:
      a second end portion of said conductive element opposite to said first end portion is not inserted into said at least one bolus;
      said at least one small bolus of soft and conductive paste or material is composed of a blend of electrically conductive nano-micro particles, an elastomer pre-polymer and a crosslinker; and
   crosslinking said elastomer pre-polymer, thereby obtaining a blend of the electrically conductive nano-micro particles and a crosslinked elastomer.

* * * * *